US010865310B2

(12) United States Patent
Matray et al.

(10) Patent No.: US 10,865,310 B2
(45) Date of Patent: *Dec. 15, 2020

(54) ULTRA BRIGHT DIMERIC OR POLYMERIC DYES

(71) Applicants: Sony Corporation, Tokyo (JP); Sony Corporation of America, New York, NY (US)

(72) Inventors: Tracy Matray, Snohomish, WA (US); Sharat Singh, Rancho Santa Fe, CA (US)

(73) Assignees: Sony Corporation of America, New York, NY (US); Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/543,827

(22) PCT Filed: May 11, 2016

(86) PCT No.: PCT/US2016/031831
§ 371 (c)(1),
(2) Date: Jul. 14, 2017

(87) PCT Pub. No.: WO2016/183185
PCT Pub. Date: Nov. 17, 2016

(65) Prior Publication Data
US 2018/0079909 A1    Mar. 22, 2018

Related U.S. Application Data

(60) Provisional application No. 62/159,771, filed on May 11, 2015.

(51) Int. Cl.
*C09B 69/10* (2006.01)
*G01N 33/58* (2006.01)

(52) U.S. Cl.
CPC .......... *C09B 69/109* (2013.01); *C09B 69/101* (2013.01); *C09B 69/102* (2013.01);
(Continued)

(58) Field of Classification Search
CPC .. C07F 9/572; C07F 9/65583; C07F 9/65586; C07F 9/6561; C07F 9/091; C07F 9/09;
(Continued)

(56) References Cited

U.S. PATENT DOCUMENTS 4,450,305 A    5/1984  Kamhi
4,476,229 A    10/1984 Fino et al.
(Continued)

FOREIGN PATENT DOCUMENTS

CN    101137735 A    3/2008
CN    102971283 A    3/2013
(Continued)

OTHER PUBLICATIONS

Babitskaya et al., "Bromoacyl Analogues of Phosphatidylcholine with Intramolecular Fluorescence Quenching and Their Use as Substrates for Continuous Monitoring of Phospholipase A2 Activity," *Applied Biochemistry and Microbiology* 40(4):351-356, 2004.
(Continued)

*Primary Examiner* — Shafiqul Haq
(74) *Attorney, Agent, or Firm* — Seed IP Law Group LLP

(57) ABSTRACT

Compounds useful as fluorescent or colored dyes are disclosed. The compounds have the following structure (I):
(Continued)

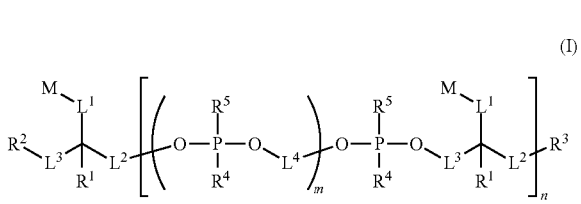

including stereoisomers, salts and tautomers thereof, wherein $R^1$, $R^2$, $R^3$, $R^4$, $R^5$, $L^1$, $L^2$, $L^3$, $L^4$, M, m and n are as defined herein. Methods associated with preparation and use of such compounds are also provided.

22 Claims, 15 Drawing Sheets

(52) U.S. Cl.
CPC ......... *C09B 69/103* (2013.01); *G01N 33/582* (2013.01); *G01N 2510/00* (2013.01)

(58) Field of Classification Search
CPC ........ C07F 9/5765; C07F 9/098; C07F 9/094; C09B 69/102; C09B 69/101; C09B 3/14; C09B 11/26; C09B 69/103; C09B 69/109; G01N 33/582; G01N 33/52; G01N 33/533
See application file for complete search history.

(56) References Cited

U.S. PATENT DOCUMENTS

| | | | |
|---|---|---|---|
| 5,053,054 | A | 10/1991 | Kirchanski et al. |
| 5,268,486 | A | 12/1993 | Waggoner et al. |
| 5,318,894 | A | 6/1994 | Pugia |
| 6,140,480 | A | 10/2000 | Kool |
| 6,171,859 | B1 | 1/2001 | Herrnstadt |
| 6,218,108 | B1 | 4/2001 | Kool |
| 6,479,650 | B1 | 11/2002 | Kool |
| 6,627,400 | B1 | 9/2003 | Singh et al. |
| 6,670,193 | B2 | 12/2003 | Kool |
| 7,172,907 | B2 | 2/2007 | Chen et al. |
| 7,423,133 | B2 | 9/2008 | Kool et al. |
| 7,897,684 | B2 | 3/2011 | Bazan et al. |
| 8,008,522 | B2 | 8/2011 | Lukhtanov et al. |
| 8,217,389 | B2 | 7/2012 | Nakano et al. |
| 8,349,308 | B2 | 1/2013 | Yurkovetskiy et al. |
| 9,085,799 | B2 | 7/2015 | Bazan et al. |
| 9,150,782 | B2 | 10/2015 | Lee et al. |
| 9,400,273 | B1 | 7/2016 | Liu et al. |
| 9,545,447 | B2 | 1/2017 | Wooley et al. |
| 9,687,291 | B2 | 6/2017 | Shimizu et al. |
| 9,689,877 | B2 | 6/2017 | Matray et al. |
| 9,765,220 | B2 | 9/2017 | Matray et al. |
| 9,851,359 | B2 | 12/2017 | Matray et al. |
| 9,884,070 | B2 | 2/2018 | Denardo et al. |
| 9,913,992 | B2 | 3/2018 | Demarest et al. |
| 10,036,754 | B2 | 7/2018 | Matray et al. |
| 10,435,563 | B2 | 10/2019 | Matray et al. |
| 2003/0054361 | A1 | 3/2003 | Heller |
| 2003/0207208 | A1 | 11/2003 | Uenishi |
| 2004/0014981 | A1 | 1/2004 | Lugade et al. |
| 2004/0138467 | A1 | 7/2004 | French et al. |
| 2004/0186278 | A1 | 9/2004 | Chen et al. |
| 2004/0224372 | A1 | 11/2004 | Li et al. |
| 2005/0054024 | A1 | 3/2005 | Lawrence |
| 2005/0123935 | A1 | 6/2005 | Haugland et al. |
| 2006/0008822 | A1 | 1/2006 | Manoharan et al. |
| 2006/0063186 | A1 | 3/2006 | Benson et al. |
| 2007/0042398 | A1 | 2/2007 | Peng et al. |
| 2007/0077549 | A1 | 4/2007 | Buller et al. |
| 2007/0148094 | A1 | 6/2007 | Uzgiris et al. |
| 2007/0269902 | A1 | 11/2007 | Beechem et al. |
| 2008/0227939 | A1 | 9/2008 | Mizoshita et al. |
| 2009/0299070 | A1 | 12/2009 | Berens et al. |
| 2010/0039684 | A1 | 2/2010 | Kolb et al. |
| 2010/0092386 | A1 | 4/2010 | Segev |
| 2010/0192312 | A1 | 8/2010 | Cremer et al. |
| 2012/0116079 | A1 | 5/2012 | Lukhtanov et al. |
| 2012/0126175 | A1 | 5/2012 | Ueno et al. |
| 2013/0059343 | A1 | 3/2013 | Cheung |
| 2013/0102021 | A1 | 4/2013 | Beacham et al. |
| 2013/0119363 | A1 | 5/2013 | Sasaki et al. |
| 2013/0137755 | A1 | 5/2013 | Segev |
| 2013/0202536 | A1 | 8/2013 | Mustaev et al. |
| 2013/0244891 | A1 | 9/2013 | Waggoner et al. |
| 2015/0110715 | A1 | 4/2015 | Eder et al. |
| 2015/0159198 | A1 | 6/2015 | McGall et al. |
| 2015/0232615 | A1 | 8/2015 | Kwiatkowski |
| 2015/0258217 | A1 | 9/2015 | Caravan et al. |
| 2016/0039850 | A1 | 2/2016 | Segev |
| 2016/0176903 | A1 | 6/2016 | Segev |
| 2016/0208100 | A1 | 7/2016 | Matray et al. |
| 2016/0264737 | A1 | 9/2016 | Bartholomew et al. |
| 2016/0341736 | A1 | 11/2016 | Matray et al. |
| 2016/0347907 | A1 | 12/2016 | Dose |
| 2017/0292957 | A1 | 10/2017 | Matray et al. |
| 2017/0326233 | A1 | 11/2017 | Demeule et al. |
| 2018/0065998 | A1 | 3/2018 | Battrell et al. |
| 2018/0163052 | A1 | 6/2018 | Matray et al. |
| 2018/0164322 | A1 | 6/2018 | Matray et al. |
| 2018/0237641 | A1 | 8/2018 | Matray et al. |
| 2019/0016898 | A1 | 1/2019 | Matray et al. |
| 2019/0136065 | A1* | 5/2019 | Singh ................. C09K 11/02 |
| 2019/0144678 | A1 | 5/2019 | Matray et al. |
| 2019/0153232 | A1 | 5/2019 | Matray et al. |
| 2019/0177549 | A1 | 6/2019 | Matray et al. |
| 2019/0300716 | A1 | 10/2019 | Matray et al. |
| 2020/0109287 | A1 | 4/2020 | Matray et al. |
| 2020/0222554 | A1 | 7/2020 | Matray et al. |
| 2020/0284798 | A1 | 9/2020 | Matray et al. |

FOREIGN PATENT DOCUMENTS

| | | |
|---|---|---|
| DE | 197 17 904 A1 | 10/1998 |
| EP | 0 708 837 A1 | 5/1996 |
| EP | 1 650 269 A2 | 4/2006 |
| EP | 1 655 317 A1 | 5/2006 |
| EP | 2 366 785 A1 | 9/2011 |
| GB | 2 456 298 A | 7/2009 |
| GB | 2554666 A | 4/2018 |
| JP | 4-282391 A | 10/1992 |
| JP | 2008-510041 A | 4/2008 |
| JP | 2008-535945 A | 9/2008 |
| JP | 2009-519595 A | 5/2009 |
| JP | 2010-508295 A | 3/2010 |
| SU | 1121931 A | 4/1988 |
| WO | 93/06482 A1 | 4/1993 |
| WO | 94/13688 A1 | 6/1994 |
| WO | 95/02700 A1 | 1/1995 |
| WO | 01/69254 A2 | 9/2001 |
| WO | 01/83502 A1 | 11/2001 |
| WO | 02/22883 A1 | 3/2002 |
| WO | 02/36832 A2 | 5/2002 |
| WO | 2006/020947 A2 | 2/2006 |
| WO | 2006/099050 A2 | 9/2006 |
| WO | 2009/015467 A1 | 2/2009 |
| WO | 2010/026957 A1 | 3/2010 |
| WO | 2013/012687 A2 | 1/2013 |
| WO | 2014/043289 A2 | 3/2014 |
| WO | 2014/102803 A1 | 7/2014 |
| WO | 2014/147642 A1 | 9/2014 |
| WO | 2014/159392 A1 | 10/2014 |
| WO | 2015/027176 A1 | 2/2015 |
| WO | 2015/109136 A2 | 7/2015 |
| WO | 2015/115415 A1 | 8/2015 |
| WO | 2016/138461 A1 | 9/2016 |
| WO | 2016/183185 A1 | 11/2016 |
| WO | 2017/173348 A1 | 10/2017 |
| WO | 2017/173355 A1 | 10/2017 |
| WO | 2018/060722 A1 | 4/2018 |

(56) References Cited

FOREIGN PATENT DOCUMENTS

| | | |
|---|---|---|
| WO | 2019/071208 A1 | 4/2019 |
| WO | 2020/210689 A1 | 10/2020 |
| WO | 2020/210692 A1 | 10/2020 |
| WO | 2020/210694 A1 | 10/2020 |

OTHER PUBLICATIONS

Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016. (8 pages).

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.

Bergstrom et al., "Potent Promise," *Innovations in Pharmaceutical Technology* 49:16-20, 2014.

Bergstrom et al., "XMT-1522 induces tumor regressions in preclinical models representing HER2-positive and HER2 low-expressing breast cancer," Mersana Therapeutics, Abstract P4-14-28, 2015, 1 page.

Chong et al., "Oxygen Quenching of Pyrene-Lipid Fluorescence in Phosphatidylcholine Vesicles—A Probe for Membrane Organization," *Biophys. J.* 47:613-621, 1985.

Kozytska et al., "Discovery of the novel, homogeneous payload platform Dolasynthen for Antibody-Drug Conjugates," Mersana Therapeutics, Abstract #272, 2018, 1 page.

Liu et al., "Detection of prostate-specific membrane antigen on HUVECs in response to breast tumor-conditioned medium," *International Journal of Oncology* 38:1349-1355, 2011.

Liu et al., "DNA-Based Micelles: Synthesis, Micellar Properties and Size-Dependent Cell Permeability," *Chem. Eur. J.* 16:3791-3797, 2010. (14 Pages).

Mersana Therapeutics, URL=http://www.mersana.com, download date Jan. 3, 2019, 9 pages.

Molotkovsky et al., "Perylenoyl- and Anthrylvinyl-Labeled Lipids as Membrane Probes," *Biochimica et Biophysica Acta* 778:281-288, 1984.

Pownall et al., "Kinetics of Spontaneous and Plasma-Stimulated Sphingomyelin Transfer," *Biochimica et Biophysica Acta* 712:169-176, 1982.

Wilson et al., "Oligodeoxyfluorosides: Strong Sequence of Dependence of Fluorescence Emission," *Tetrahedron* 63(17):3427-3433, 2007. (18 Pages).

Yurkovetskiy et al., "Advantages of Polyacetal Polymer-based Antibody Drug Conjugates: Application to Low Expression Targets," Mersana Therapeutics, technical paper #2645, 2014, 1 page.

CAPLUS Accession No. 1975:171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

"What is an Analyte?," Google Search, dated Mar. 22, 2018, retrieved from https://www.google.com/search?q=what+is+an+analyte&rlz=1C1GCEB_enUS775US775&oq=what+is+an+analyte&aqs=chrome..69i57j0l5.32321j0j7&s . . . 2 pages.

Arian et al., "1,9-Dialkoxyanthracene as a $^1O_2$-Sensitive Linker," *J. Am. Chem. Soc.* 133:3972-3980, 2011.

Becker et al., "New Thermotropic Dyes Based on Amino-Substituted Perylendicarboximides," *Chem. Eur. J.* 6(21):3984-3990, 2000.

Braeckmans et al., "Three-Dimensional Fluorescence Recovery after Photobleaching with the Confocal Scanning Laser Microscope," *Biophysical Journal* 85:2240-2252, 2003.

Braga et al., "Intracellular Macromolecular Mobility Measured by Fluorescence Recovery after Photobleaching with Confocal Laster Scanning Microscopes," *Molecular Biology of the Cell* 15:4749-4760, 2004.

Brinkley, "A Brief Survey of Methods for Preparing Protein Conjugates with Dyes, Haptens, and Cross-Linking Reagents," *Bioconjugate Chem* 3:2-13, 1992.

Dai et al., "DNA-polyfluorophore excimers as sensitive reporters for esterases and lipases," *Chem. Commun.* 46:1221-1223, 2010.

Divittorio et al., "Synthetic peptides with selective affinity for apoptotic cells," *Organic & Biomolecular Chemistry* 4(10):1966-2006.

Gao et al., "Libraries of Composite Polyfluors Built from Fluorescent Deoxyribosides," *Journal of the American Chemical Society* 124(39):11590-11591, 2002.

Gao et al., "Modified DNA Analogues That Sense Light Exposure with Color Changes," *J. Am. Chem. Soc.* 126:12748-12749, 2004.

Gordon et al., "Analysis of Simulated and Experimental Fluorescence Recovery After Photobleaching. Data for Two Diffusing Components," *Biophysical Journal* 68:766-778, 1995.

Hanhela et al., "Synthesis and Evaluation of Fluorescent Materials for Colour Control of Peroxyolate Chemiluminescene. III Yellow and Red Fluorescent Emitters," *Aust. J. Chem.* 34:1701-1717, 1981.

Haraguchi, "Live Cell Imaging: Approaches for Studying Protein Dynamics in Living Cells," *Cell Structure and Function* 27:333-334, 2002.

Koo et al., "Fluorescent DNA chemosensors: identification of bacterial species by their volatile metabolites," *Chem. Commun.* 47:11435-11437, 2011.

Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.

Nussbaumer et al., "Amplification of Chirality by Supramolecular Polymerization of Pyrene Oligomers," *Angew. Chem. Int. Ed.* 50:5490-5494, 2011.

PubChem, "US20100012929A1-20100121-C00010_4," SID No. 140452858, retrieved Mar. 29, 2016 from URL https://pubchem.ncbi.nlm.nih.gov/substance/140452858, 6 pages.

Wang et al., "Cruciforms: Assembling Single Crystal Micro- and Nanostructures from One to Three Dimensions and Their Applications in Organic Field-Effect Transistors," *Chem. Mater.* 21:2840-2845, 2009.

Wang et al., "DNA Polyfluorophores for Real-Time Multicolor Tracking of Dynamic Biological Systems," *Angew. Chem. Int. Ed.* 51:7176-7180, 2012.

Wilson et al., "Efficient Quenching of Oligomeric Fluorophores on a DNA Backbone," *J. Am. Chem. Soc.* 129:15426-15427, 2007.

RN 230952-79-1, Registry Database Compound (1999).

Kozma et al., "Fluorescent Ligands for Adenosine Receptors," *Bioorganic & Medicinal Chemistry Letters* 23: 26-36, 2013.

Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.

Petreus et al., "Polyester imides containing main-chain phosphorus," *Revue Roumaine de Chimie* 34(8):971-978, 1994 (with English Abstract) (9 pages).

Singh et al., "Multiplexed measurement of membrane protein populations," Caplus 2003:769075, 2003. (2 pages).

U.S. Appl. No. 16/639,496, filed Feb. 14, 2020.
U.S. Appl. No. 16/639,499, filed Feb. 14, 2020.
U.S. Appl. No. 16/763,922, filed May 13, 2020.
U.S. Appl. No. 16/879,572, filed May 20, 2020.

Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.

Jain et al. "Current ADC Linker Chemistry," *Pharm. Res.* 32:3526-3540, 2015.

Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.

Beaucage et al., "The Functionalization of Oligonucleotides Via Phosphoramidite Derivatives," *Tetrahedron* 49(10):1925-1963, 1993.

Chattopadhyay et al., "Brilliant Violet Fluorophores: A New Class of Ultrabright Fluorescent Compounds for Immunofluorescence Experiments," *Cytometry Part A 81A*:456-466, 2012.

(56) References Cited

OTHER PUBLICATIONS

Chekalin et al., "Technology of organic dyes and intermediates," Textbook, 2nd edition, L. Chemistry, pp. 225-453, 1980.

Cuppoletti et al., "Oligomeric fluorescent labels for DNA," *Bioconjug. Chem.* 16(3):528-534, 2005.

Dubrovsky, "Semiconductor nanoparticles as reporters in multiplexed immunoassay and cell analysis," *International Journal of Nanoscience* 8(1 & 2):163-167, 2009.

Luo et al., "Sensitive and rapid quantification of C-reactive protein using quantum dot-labeled microplate immunoassay," *Journal of Translational Medicine* 10(24):1-9, 2012.

Paris et al., "Probing DNA sequences in solution with a monomer-excimer fluorescence color change," *Nucleic Acids Research* 26(16):3789-3793, 1998.

Ren et al., "An Antisense Oligodeoxynucleotide-Doxorubicin Conjugate: Preparation and Its Reversal Multidrug Resistance of Human Carcinoma Cell Line in Vitro," *Nucleosides, Nucleotides & Nucleic Acids* 23(10):1595-1607, 2004.

Stuart et al., "Site-Specific Dna-Doxorubicin Conjugates Display Enhanced Cytotoxicity to Breast Cancer Cells," *Bioconjugate Chemistry* 25406-413, 2014.

Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010 23 pages).

Tram et al., "Oligonucleotide Labeling Using Bodipy Phosphoramidite," *Nucleosides, Nucleotides & Nucleic Acids* 30(1):1-11, 2011.

Avirah et al., "Infrared Absorbing Croconaine Dyes: Synthesis and Metal Ion Binding Properties," *J. Org. Chem.* 73(1):274-279, 2008.

Li et al., "Responsive nanogel-based dual fluorescent sensors for temperature and $Hg^{2+}$ ions with enhanced detection sensitivity," *J. Mater. Chem.* 20:10716-10723, 2010.

Stewart et al., "The Fluorescence of a Chelating Two-Photon-Absorbing Dye is Enhanced with the Addition of Transition Metal Ions but Quenched in the Presence of Acid," *Proc. Of SPIE* 9939:99304, 2016 (10 pages).

Zhang et al., "FRET Imaging of Enzyme-Responsive HPMA Copolymer Conjugate," *Macromolecular Bioscience* 17:1600215, 2017 (8 pages).

\* cited by examiner

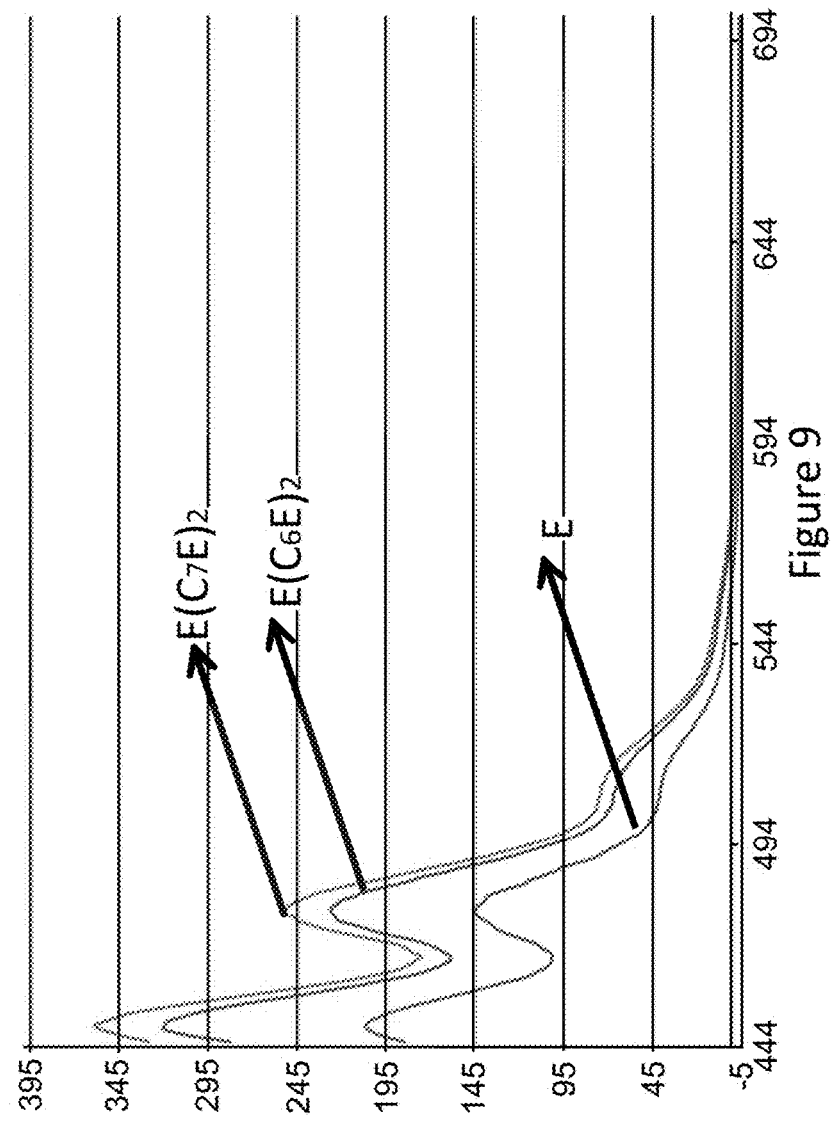

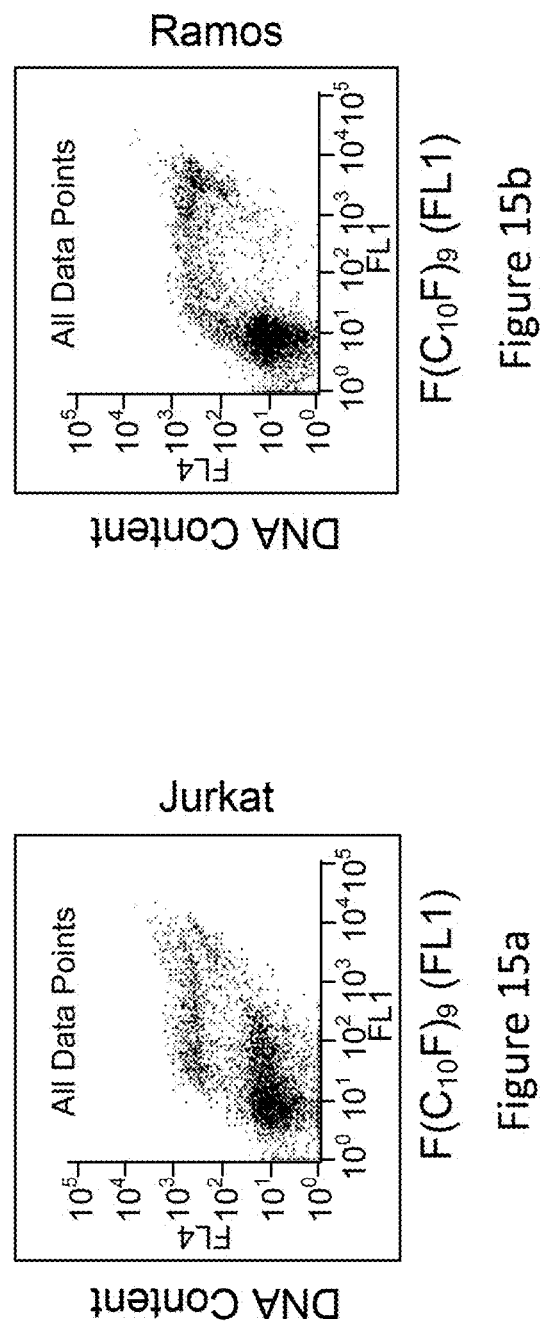

ULTRA BRIGHT DIMERIC OR POLYMERIC DYES

BACKGROUND

Field

The present invention is generally directed to dimeric and polymeric fluorescent or colored dyes, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes ("brighter") are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the dimeric and polymeric dyes did not achieve the desired increase in brightness.

There is thus a need in the art for water soluble dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, the present invention is generally directed to compounds useful as water soluble, fluorescent or colored dyes and probes that enable visual detection of analyte molecules, such as biomolecules, as well as reagents for their preparation. Methods for visually detecting an analyte molecule using the dyes are also described.

Embodiments of the presently disclosed dyes include two or more fluorescent and/or colored moieties covalently linked by a linker which is typically charged at pH's ranging from 1-14, for example at pH's above 7. In contrast to previous reports of dimeric and/or polymeric dyes, the present dyes are significantly brighter than the corresponding monomeric dye compound. While, not wishing to be bound by theory, it is believed that electrostatic repulsion of the charged linker acts to maintain the spatial distant between the fluorescent and/or colored moieties, and thus intramolecular fluorescence quenching is reduced and/or eliminated.

The water soluble, fluorescent or colored dyes of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In one embodiment, compounds having the following structure (I) are provided:

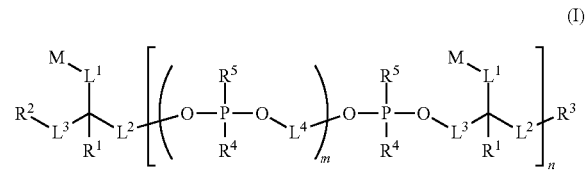

(I)

or a stereoisomer, tautomer or salt thereof, wherein $R^1$, $R^2$, $R^3$, $R^4$, $R^5$, $L^1$, $L^2$, $L^3$, $L^4$, M, m and n are as defined herein.

In another embodiment, a method for staining a sample is provided, the method comprises adding to said sample a representative compound as described herein in an amount sufficient to produce an optical response when said sample is illuminated at an appropriate wavelength.

In still other embodiments, the present disclosure provides a method for visually detecting an analyte molecule, comprising:

(a) providing a representative compound described herein; and (b) detecting the compound by its visible properties.

Other disclosed methods include a method for visually detecting a biomolecule, the method comprising:

(a) admixing any of the disclosed compounds with one or more biomolecules; and (b) detecting the compound by its visible properties.

Other embodiments are directed to a composition comprising any one of the disclosed compounds and one or more biomolecules. Use of such composition in analytical methods for detection of the one or more biomolecules is also provided.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 9 provides additional fluorescence emission spectra of representative compounds relative to the parent fluorophore.

FIGS. 15a and 15b illustrate patterns of proliferative effects of dead and apoptotic cells.

DETAILED DESCRIPTION

Figure 1:
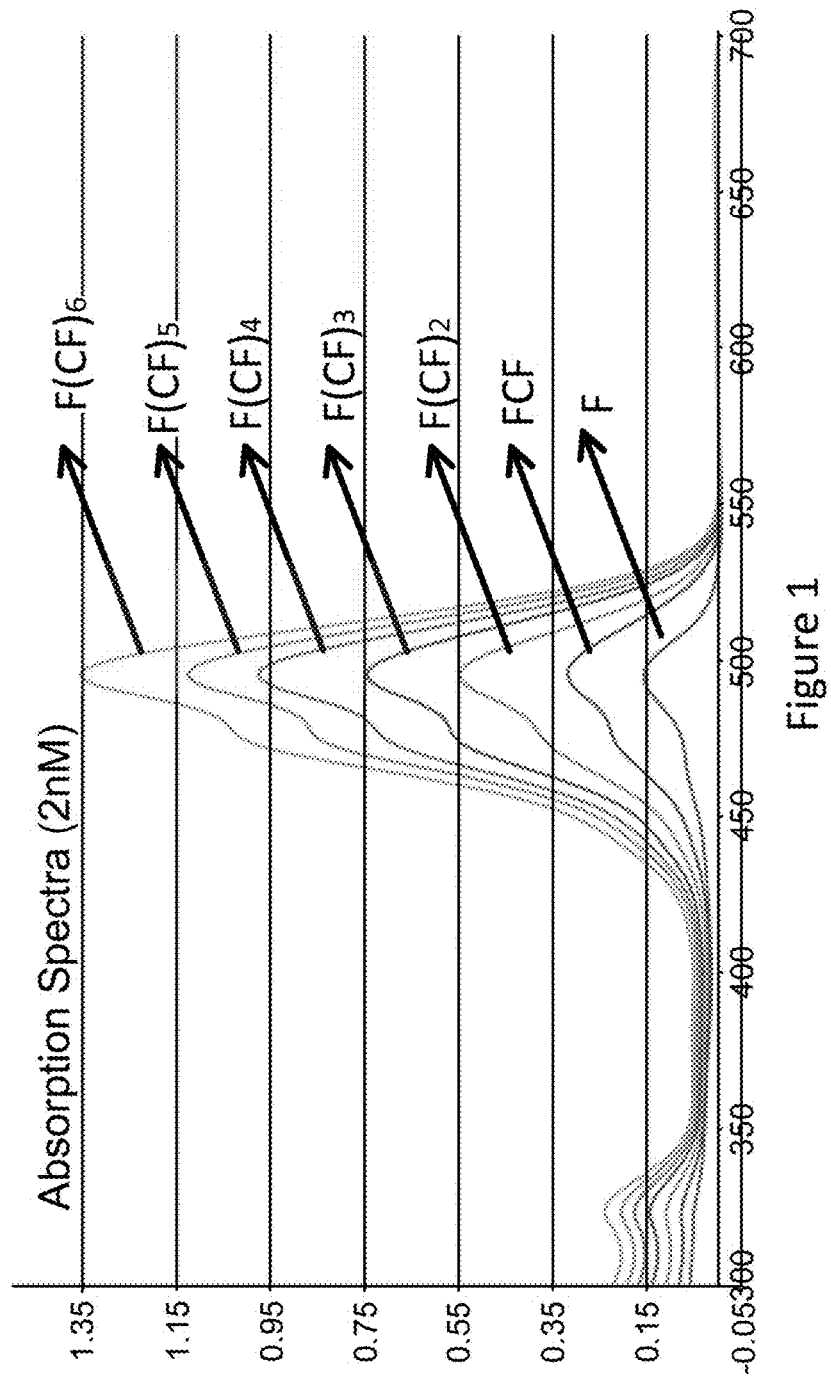
FIG. 1 provides UV absorbance spectra for comparative dye compounds.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ group.
"Carboxy" refers to the —CO$_2$H group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —NO$_2$ group.
"Oxo" refers to the =O substituent group.
"Sulfhydryl" refers to the —SH group.
"Thioxo" refers to the =S group.
"Alkyl" refers to a straight or branched hydrocarbon chain group consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. An "alkenyl" is an alkyl comprising at least one carbon-carbon double bond. An "alkynyl" is an alkyl comprising at least one carbon-carbon triple bond. Unless stated otherwise specifically in the specification, alkyl, alkenyl and alkynyl groups are optionally substituted.

"Alkylene" or "alkylene chain" refers to a straight or branched divalent hydrocarbon chain linking the rest of the molecule to a substituent group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. An "alkenylene" is an alkylene comprising at least one carbon-carbon double bond. An "alkynylene" is an alkylene comprising at least one carbon-carbon triple bond. The alkylene chain is attached to the rest of the molecule through a single or double bond and to the substituent group through a single or double bond. The points of attachment of the alkylene chain to the rest of the molecule and to the substituent group can be through one carbon or any two carbons within the chain. Unless stated otherwise specifically in the specification, alkylene, alkenylene and alkynylene are optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments and alkylether is substituted with an alcohol or phosphate.

"Alkoxy" refers to a group of the formula —OR$_a$ where R$_a$ is an alkyl group as defined above containing one to twelve carbon atoms. Unless stated otherwise specifically in the specification, an alkoxy group is optionally substituted.

"Heteroalkylene" refers to an alkylene group comprising at least one heteroatom (e.g., N, O or S). In some embodiments, the heteroatom is within the alkylene chain (i.e., the heteroalkylene comprises at least one carbon-heteroatom-carbon bond. In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). "Heteroalkenylene" is a heteroalkylene comprising at least one carbon-carbon double bond. "Heteroalkynylene" is a heteroalkylene comprising at least one carbon-carbon triple bond. Unless stated otherwise specifically in the specification, heteroalkylene, heteroalkenylene and heteroalkynylene are optionally substituted.

An exemplary heteroalkylene linking group is illustrated below:

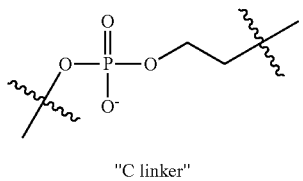 [SMILES: *CCOP(=O)([O-])O*]

"C linker"

Multimers of the above C-linker are included in various embodiments of heteroalkylene linkers.

"Heteroatomic" in reference to a "heteroatomic linker" refers to a linker group consisting of one or more heteroatom. Exemplary heteroatomic linkers include single atoms selected from the group consisting of O, N, P and S, and multiple heteroatoms for example a linker having the formula —P(O⁻)(=O)O— or —OP(O⁻)(=O)O— and multimers and combinations thereof.

"Phosphate" refers to the —OP(=O)($R_a$)$R_b$ group, wherein $R_a$ is OH, O or $OR_E$; and $R_b$ is OH, O⁻, $OR_E$, a thiophosphate group or a further phosphate group, wherein $R_c$ is a counter ion (e.g., Na+ and the like).

"Phosphoalkyl" refers to the —OP(=O)($R_a$)$R_b$ group, wherein $R_a$ is OH, O⁻ or $OR_c$⁻; and $R_b$ is —Oalkyl, wherein $R_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Phosphoalkylether" refers to the —OP(=O)($R_a$)$R_b$ group, wherein $R_a$ is OH, O⁻ or $OR_c$; and $R_b$ is —Oalkylether, wherein $R_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphate" refers to the —OP(=$R_a$)($R_b$)$R_c$ group, wherein $R_a$ is O or S; $R_b$ is OH, O⁻, S⁻, $OR_d$ or $SR_d$; and $R_c$ is OH, SH, O⁻, S⁻, $OR_d$, $SR_d$, a phosphate group or a further thiophosphate group, wherein $R_d$ is a counter ion (e.g., Na+ and the like) and provided that: i) $R_a$ is S; ii) $R_b$ is S⁻ or $SR_d$⁻; iii)$R_c$ is SH, S⁻ or $SR_d$; or iv) a combination of i), ii) and/or iii).

"Thiophosphoalkyl" refers to the —OP(=$R_a$)($R_b$)$R_c$ group, wherein $R_a$ is O or S; $R_b$ is OH, O⁻, S⁻, $OR_d$ or $SR_d$⁻; and $R_c$ is —Oalkyl, wherein $R_d$ is a counter ion (e.g., Na+ and the like) and provided that: $R_a$ is S or $R_b$ is S⁻ or $SR_d$; or provided that $R_a$ is S and $R_b$ is S⁻ or $SR_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphoalkylether" refers to the —OP(=$R_a$)($R_b$)$R_c$ group, wherein $R_a$ is O or S, $R_b$ is OH, O⁻, S⁻, $OR_d$ or $SR_d$; and $R_c$ is —Oalkylether, wherein $R_d$ is a counter ion (e.g., Na+ and the like) and provided that: $R_a$ is S or $R_b$ is S⁻ or $SR_d$; or provided that $R_a$ is S and $R_b$ is S⁻ or $SR_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1- dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkenyl, alkynyl, alkylene, alkenylene, alkynylene, heteroalkylene, heteroalkenylene, heteroalkynylene, alkoxy, alkylether, phosphate, phosphoalkyl, phosphoalkylether, thiophosphate, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening double bond. For example, 1,3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (i.e., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively.

Isotopically-labeled compounds of structure (I) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. The present invention includes all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

The compounds of the invention, or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as fluorescent and/or colored dyes in various analytical methods are provided. In general terms, embodiments of the present invention are directed to dimers and higher polymers of fluorescent and/or colored moieties. The fluorescent and or colored moieties are linked by linkers having multiple positively charged moieties or multiple negatively charges moieties at the pH at which an assay is conducted. Without wishing to be bound by theory, it is believed electrostatic repulsion of the multiple charged moieties within the linker helps to maintain sufficient spatial distance between the fluorescent and/or colored moieties such that intramolecular quenching is reduced or eliminated, this resulting in a dye compound having a high molar "brightness" (e.g., high fluorescence emission).

For example, the linker may comprise phosphate and/or thiophosphate moieties when a negative charge is desired. When positive charges are desired, linking groups containing quaternary amine groups and/or other groups capable of holding a positive charge may be used. Accordingly, in some embodiments the compounds have the following structure (A):

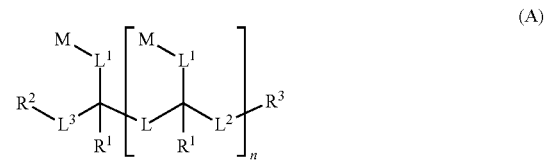

(A)

wherein L is a linker comprising multiple positively charged moieties or multiple negatively charged moieties, and the other variables are as defined for structure (I). By "charged moieties" it is understood that the moieties will be charged at certain pH's, for example at the pH at which an assay employing the compound is performed, but it is not a requirement that the "charged moieties" be charged at all pH's.

In some other embodiments, the compounds have the following structure (I):

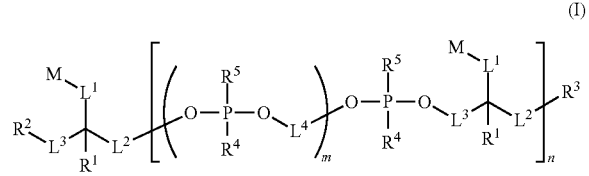

(I)

or a stereoisomer, tautomer or salt thereof, wherein:

M is, at each occurrence, independently a moiety comprising two or more carbon-carbon double bonds and at least one degree of conjugation;

$L^1$, $L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene, alkenylene, alkynylene, heteroalkylene, heteroalkenylene or heteroalkynylene linker;

$R^1$ is, at each occurrence, independently H, alkyl or alkoxy;

$R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O$^-$, S$^-$, OR$_d$ or SR$_d$; $R_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether;

$R^4$ is, at each occurrence, independently OH, SH, O$^-$, S$^-$, OR$_d$ or SR$_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

$R^d$ is a cation;

m is, at each occurrence, independently an integer of zero or greater, provided that at least one occurrence of m is an integer of three or greater; and n is an integer of one or greater.

In some embodiments, m is, at each occurrence, independently an integer of three or greater.

In some embodiments, $L^1$, $L^2$ and $L^3$ are, at each occurrence, independently optional alkylene or heteroalkylene linkers.

In some other embodiments of the compound of structure (I):

M is, at each occurrence, independently a moiety comprising two or more carbon-carbon double bonds and at least one degree of conjugation;

$L^1$, $L^2$ and $L^3$ are, at each occurrence, independently optional alkylene or heteroalkylene linkers;

$L^4$ is, at each occurrence, independently an alkylene, alkenylene, alkynylene, heteroalkylene, heteroalkenylene or heteroalkynylene linker up to twenty atoms in length;

$R^1$ is, at each occurrence, independently H, alkyl or alkoxy;

$R^2$ and $R^3$ are each independently H, OH, —OP(=$R_a$)($R_b$)$R_c$, Q, a linker comprising a covalent bond to Q, a linker comprising a covalent bond to an analyte molecule or a linker comprising a covalent bond to a solid support, wherein: $R_a$ is O or S; $R_b$ is OH, SH, O$^-$, S$^-$, OR$_d$ or SR$_d$; $R_c$ is OH, SH, O$^-$, S$^-$, OR$_d$, SR$_d$, phosphate, thiophosphate, phosphoalkyl, thiophosphoalkyl, phosphoalkylether or thiophosphoalkylether;

$R^4$ is, at each occurrence, independently OH, SH, O$^-$, S$^-$, OR$_d$ or SR$_d$;

$R^5$ is, at each occurrence, independently oxo, thioxo or absent;

Q is a moiety capable of bonding with an analyte molecule or a solid support;

$R_d$ is a cation;

m is, at each occurrence, independently an integer of zero or greater, provided that at least one occurrence of m is an integer of three or greater; and n is an integer of one or greater.

In some embodiments, the compound has the following structure (IA):

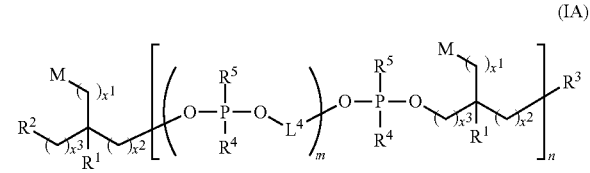

wherein $x^1$, $x^2$ and $x^3$ are, at each occurrence, independently an integer from 0 to 6.

The $L^4$ linker can be selected, along with other variables, to provide the desired fluorescence and/or color ("tune" the fluorescence and/or color). In some embodiments, $L^4$ is a linker up to 20 atoms in length, up to 13 atoms in length, for example up to 10 atoms in length or up to 6 atoms in length. In certain embodiments, $L^4$ does not include disulfide bonds. In other embodiments, $L^4$ is, at each occurrence, independently $C_1$-$C_6$ alkylene or $C_2$-$C_6$ alkynylene. In some embodiments, $L^4$ is a two-carbon linker.

In some other different embodiments, the compound has the following structure (IB):

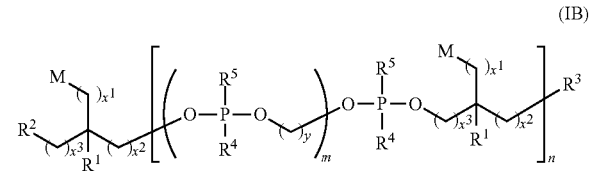

wherein:

$x^1$, $x^2$ and $x^3$ are, at each occurrence, independently an integer from 0 to 6; and y is, at each occurrence, independently an integer from 1 to 6.

In certain embodiments of the foregoing y is 2. In other embodiments, $x^1$, $x^2$ and $x^3$ are each 1 at each occurrence. In some different embodiments, $x^2$ is 0 and $x^3$ is 1 at each occurrence.

In still other embodiments, $R^4$ is, at each occurrence, independently OH, O$^-$ or OR$_d$. It is understood that "OR$_d$" and "SR$_d$" are intended to refer to O$^-$ and S$^-$ associated with a cation. For example, the disodium salt of a phosphate group may be represented as:

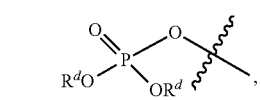

where $R^d$ is sodium (Na$^+$).

In further of the foregoing embodiments, $R^5$ is, at each occurrence, oxo.

In some other embodiments, the compound has one of the following structures (IB') or (IB"):

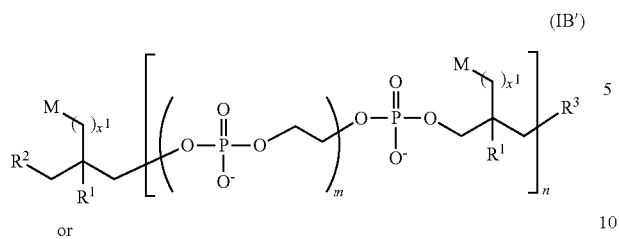
(IB′)

or

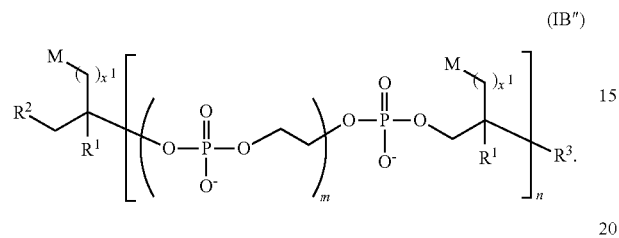
(IB″)

In any embodiments of the foregoing, $R^1$ is H.

In different embodiments, $R^2$ and $R^3$ are each independently OH or $-OP(=R_a)(R_b)R_c$. For example, in some embodiments $R^2$ and $R^3$ are each independently OH or $-OP(=R_a)(R_b)R_c$, wherein $R_a$ is O, $R_b$ is OH, O⁻ or $OR^d$; $R_c$ is OH, O⁻, $OR^d$, phosphate, thiophosphate, phosphoalkyl, thiophosphoalkyl, phosphoalkylether or thiophosphoalkylether; and $R^d$ is a counter ion.

In still other different embodiments, one of $R^2$ or $R^3$ is OH or $-OP(=R_a)(R_b)R_c$, and the other of $R^2$ or $R^3$ is Q or a linker comprising a covalent bond to Q. For example, in some embodiments one of $R^2$ or $R^3$ is OH or $-OP(=R_a)(R_b)R_c$, and the other of $R^2$ or $R^3$ is Q or a linker comprising a covalent bond to Q, wherein $R^a$ is O, $R_b$ is OH, O⁻ or $OR^d$; $R_c$ is OH, O⁻, $OR^d$, phosphate, thiophosphate, phosphoalkyl, thiophosphoalkyl, phosphoalkylether or thiophosphoalkylether; and $R^d$ is a counter ion.

In still other embodiments, Q is or comprises a moiety capable of bonding with an analyte molecule or a solid support. In certain embodiments, Q provides a means of connecting the compound of structure (I) to an analyte molecule or a solid support (e.g., by a covalent bond). For example, in some embodiments Q is or comprises a reactive group capable of forming a covalent bond with an analyte molecule or a solid support. In this regard the type of Q group and connectivity of the Q group to the remainder of the compound of structure (I) is not limited. In certain embodiments, the Q is a moiety which is not susceptible to hydrolysis under aqueous conditions, but is sufficiently reactive to form a bond with a corresponding group on an analyte molecule or solid support (e.g., an amine).

Certain embodiments of compounds of structure (I) comprises Q groups commonly employed in the field of bioconjugation. For example in some embodiments, Q is or comprises a nucleophilic reactive group, an electrophilic reactive group or a cycloaddition reactive group. In some more specific embodiments, Q is or comprises sulfhydryl, disulfide, activated ester, isothiocyanate, azide, alkyne, alkene, diene, dienophile, acid halide, sulfonyl halide, phosphine, α-haloamide, biotin, amino or a maleimide. In some embodiments, the activated ester is an N-succinimide ester, imidoester or polyflourophenyl ester. In other embodiments, the alkyne is an alkyl azide or acyl azide.

Exemplary Q moieties are provided in Table I below.

TABLE 1

Exemplary Q Moieties

| Structure | Class |
|---|---|
| —SH | Sulfhydryl |
| —N=C=S | Isothiocyanate |
| imidoester structure with $NH_2^+Cl^-$ | Imidoester |
| acyl azide structure | Acyl Azide |
| tetrafluorophenyl ester | Activated Ester |
| sulfo-nitrophenyl ester | Activated Ester |
| sulfo-SMCC type structure | Activated Ester |
| N-hydroxysuccinimide ester | Activated Ester |
| sulfo-NHS ester | Activated Ester |
| —S(O)₂—X, X = halo | Sulfonyl halide |

TABLE 1-continued

Exemplary Q Moieties

| Structure | Class |
|---|---|
| (maleimide structure) | Maleimide |
| (maleimide-cyclohexyl-amide structure) | Maleimide |
| (α-haloimide structure), X = halo | α-haloimide |
| (pyridyl disulfide structure) | Disulfide |
| (phosphine structure with PPh₂ and methyl ester) | Phosphine |
| —N₃ | Azide |
| (alkyne structure) | Alkyne |
| (biotin structure) | Biotin |
| (diene structure) | Diene |
| (alkene structure) | Alkene/dienophile |

TABLE 1-continued

Exemplary Q Moieties

| Structure | Class |
|---|---|
| (alkene-EWG structure), EWG = electron withdrawing group | Alkene/dienophile |
| —NH₂ | Amino |

It should be noted that in some embodiments, wherein Q is SH, the SH moiety will tend to form disulfide bonds with another sulfhydryl group on another compounds of structure (I). Accordingly, some embodiments include compounds of structure (I), which are in the form of disulfide dimers, the disulfide bond being derived from SH Q groups.

In some other embodiments, one of $R^2$ or $R^3$ is OH or —OP(=$R_a$)($R_b$)$R_c$, and the other of $R^2$ or $R^3$ is a linker comprising a covalent bond to an analyte molecule or a linker comprising a covalent bond to a solid support. In some different embodiments, one of $R^2$ or $R^3$ is OH or —OP(=$R_a$)($R_b$)$R_c$, and the other of $R^2$ or $R^3$ is a linker comprising a covalent bond to an analyte molecule or a linker comprising a covalent bond to a solid support, wherein $R^a$ is O, $R_b$ is OH, O⁻ or $OR^d$; R is OH, O⁻, $OR^d$, phosphate, thiophosphate, phosphoalkyl, thiophosphoalkyl, phosphoalkylether or thiophosphoalkylether; and $R^d$ is a counter ion. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The value form is another variable that can be selected based on the desired fluorescence and/or color intensity. In some embodiments, m is, at each occurrence, independently an integer from 3 to 10. In other embodiments, m is, at each occurrence, independently an integer from 7 to 9.

The fluorescence intensity can also be tuned by selection of different values of n. In certain embodiments, n is an integer from 1 to 100. In other embodiments, n is an integer from 1 to 10.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. M may be attached to the remainder of the molecule from any position (i.e., atom) on M. One of skill in the art will recognize means for attaching M to the remainder of molecule.

In some embodiments, M is a fluorescent or colored moiety. Any fluorescent and/or colored moiety known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9,10-ethynylanthracene or ter-naphthyl moiety. In other embodiments, $M^1$ is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrromethenebroron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or derivative thereof. In some other embodiments, $M^1$ has one of the following structures:

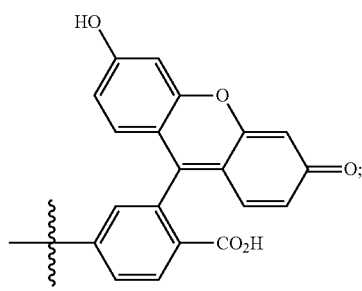

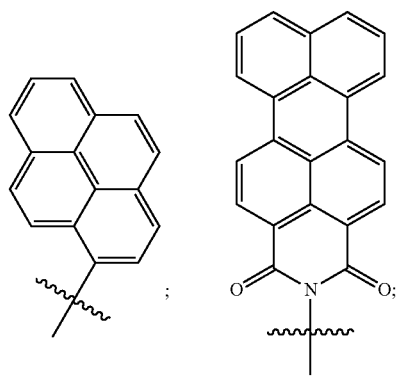

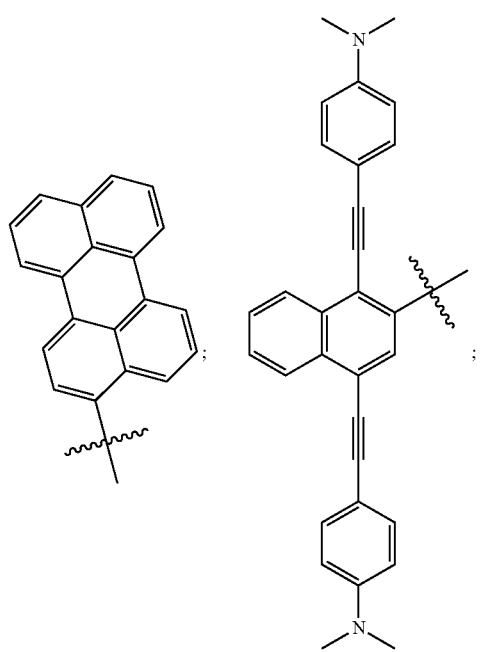

-continued
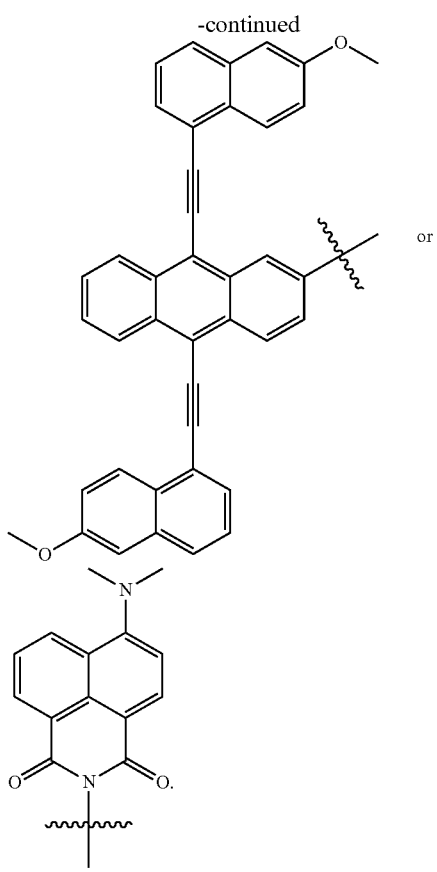
or
In some other embodiments, M¹ has the following structure:
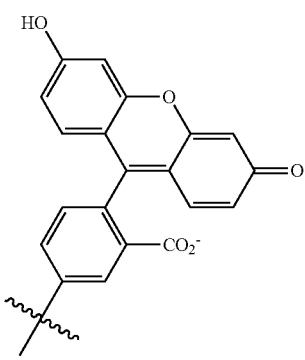
In some specific embodiments, the compound is a compound selected from Table 2:
TABLE 2
Exemplary Compounds
| Name | Structure |
|---|---|
| FC₃F | |
| FC₄F | |
| FC₅F | |

TABLE 2-continued
Exemplary Compounds
| Name | Structure |
|---|---|
| FC$_6$F | 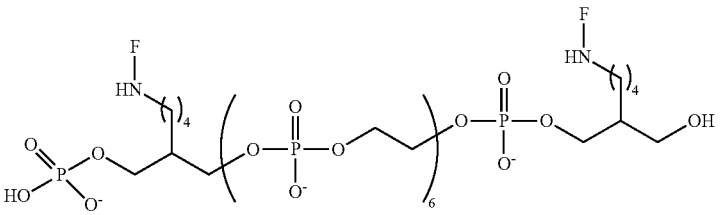 |
| FC$_7$F | 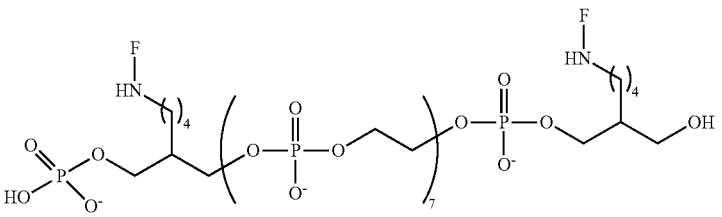 |
| FC$_8$F | 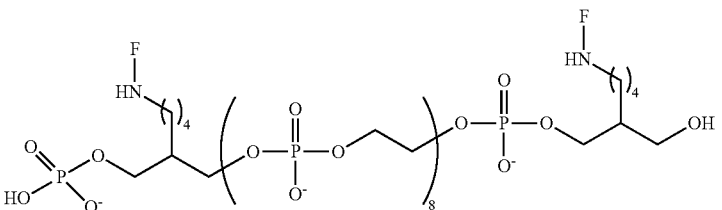 |
| FC$_9$F | 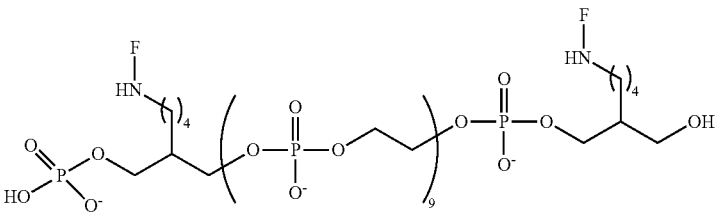 |
| YC$_3$Y | 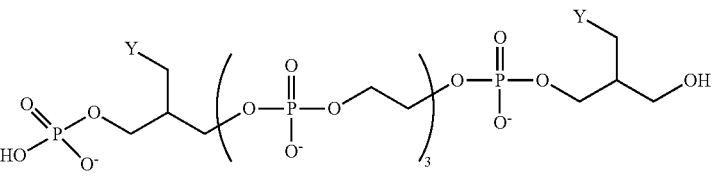 |
| YC$_4$Y | 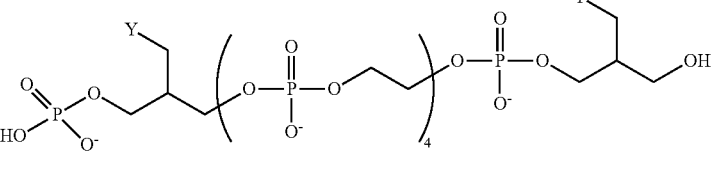 |
| YC$_5$Y | 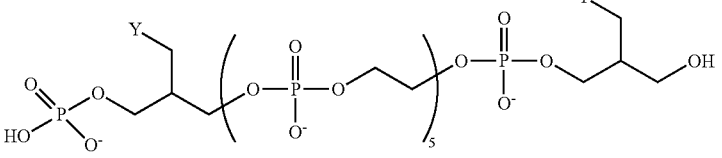 |

TABLE 2-continued

Exemplary Compounds

| Name | Structure |
|---|---|
| YC$_6$Y | 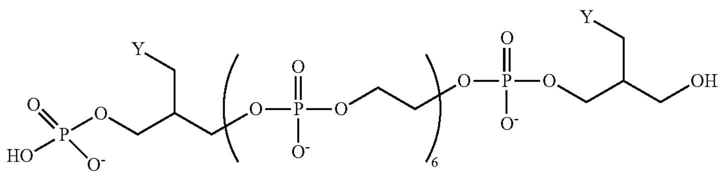 |
| YC$_3$FC$_3$Y | 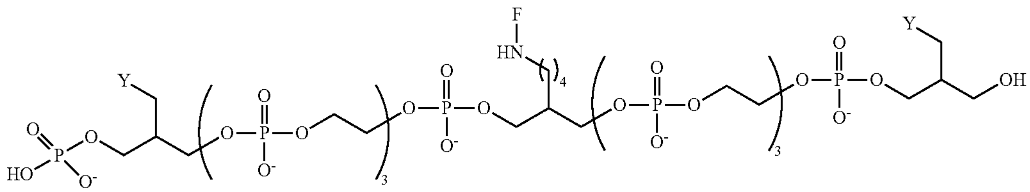 |
| YC$_4$FC$_4$Y | 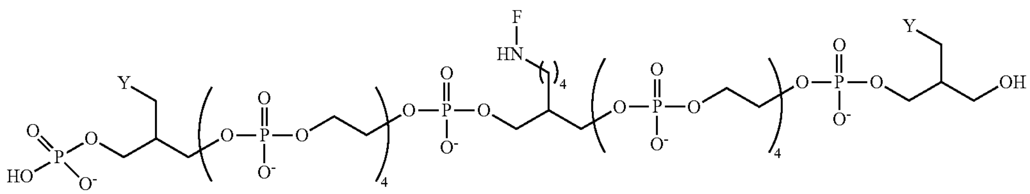 |
| F(C$_4$F)$_2$ | 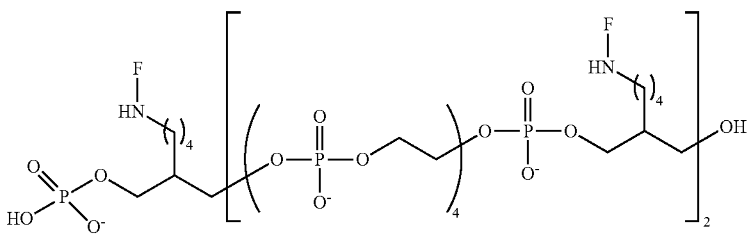 |
| F(C$_4$F)$_3$ | 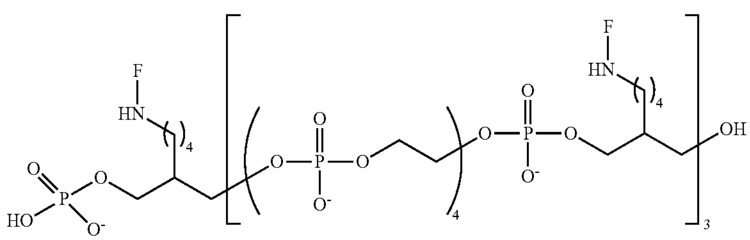 |
| F(C$_4$F)$_4$ | 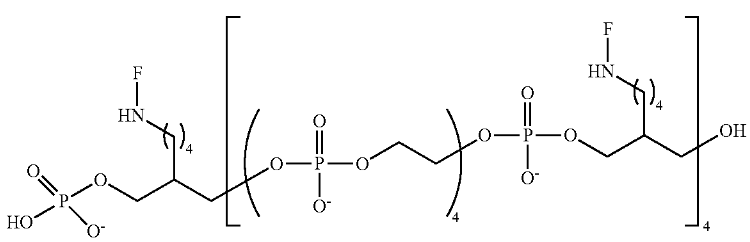 |
| F(C$_4$F)$_5$ | 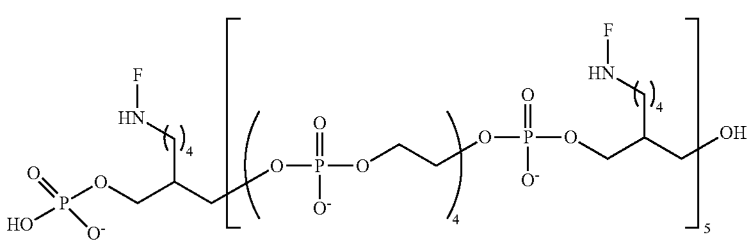 |

TABLE 2-continued

Exemplary Compounds

| Name | Structure |
|---|---|
| F(C$_7$F)$_2$ | 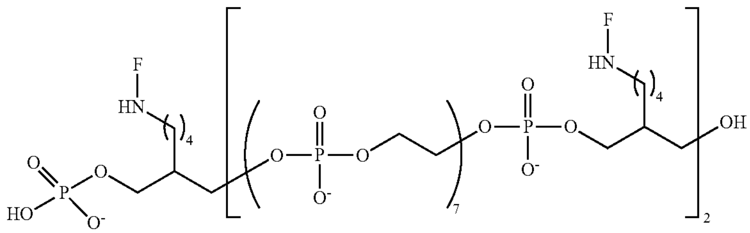 |
| F(C$_7$F)$_3$ | 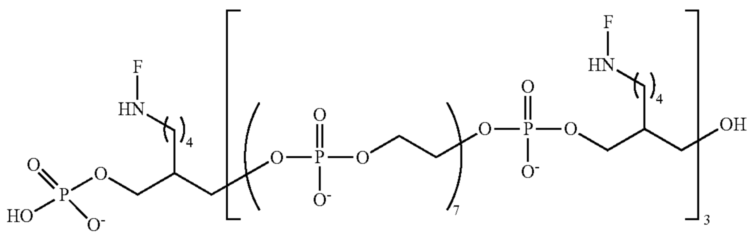 |
| F(C$_7$F)$_4$ | 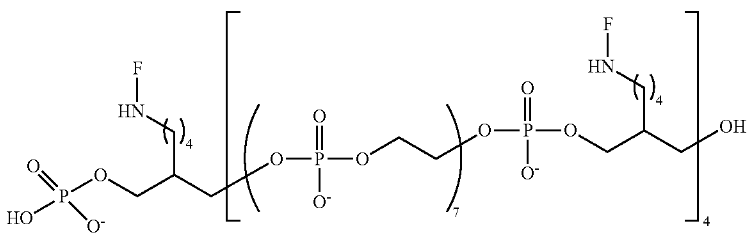 |
| F(C$_7$F)$_5$ | 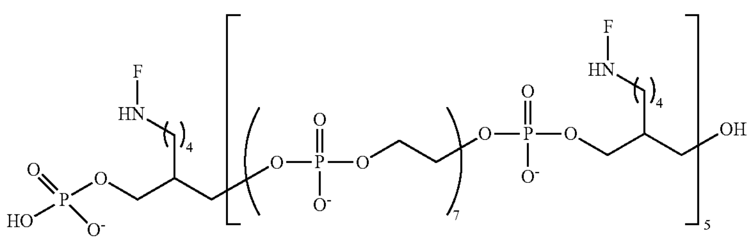 |
| F(C$_7$F)$_9$ | 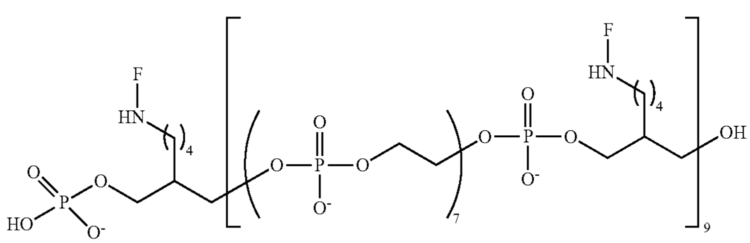 |
| F(C$_{10}$F)$_9$ | 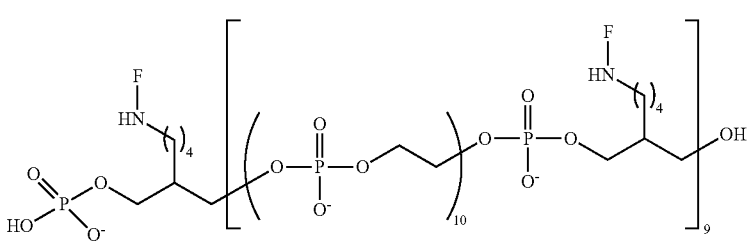 |

TABLE 2-continued
Exemplary Compounds
| Name | Structure |
|---|---|
| F(C₁₀F)₉SH | 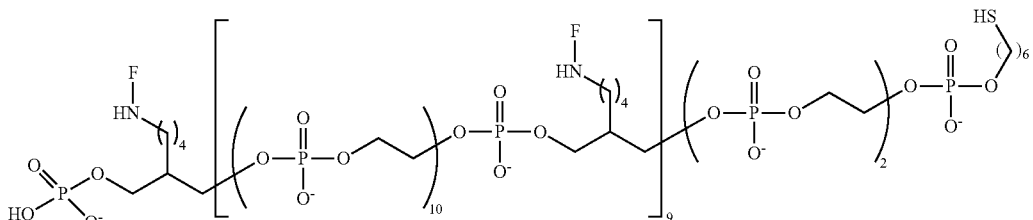 |
| EC₃E | 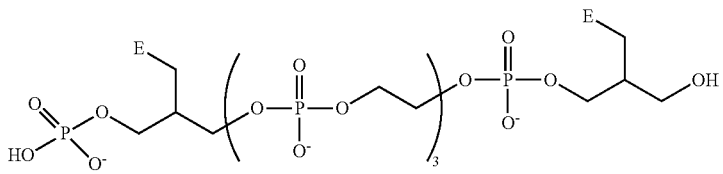 |
| EC₄E | 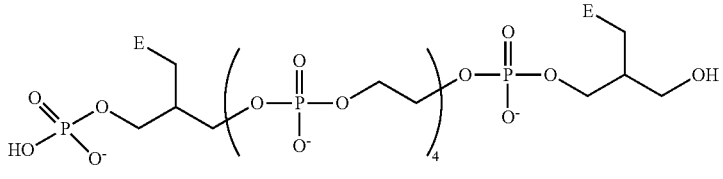 |
| EC₅E | 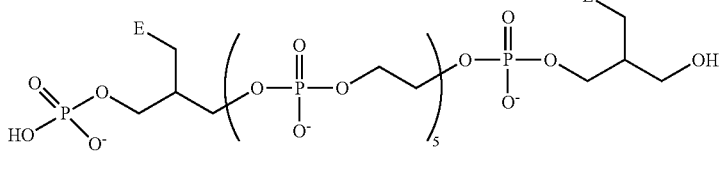 |
| EC₆E | 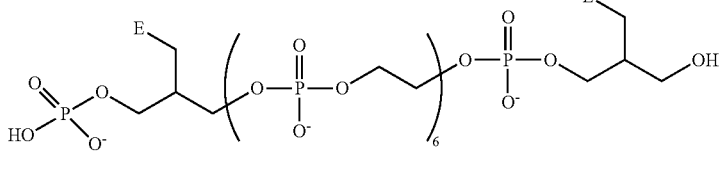 |
| EC₇E | 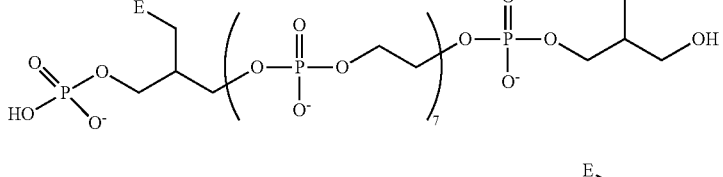 |
| EC₈E | 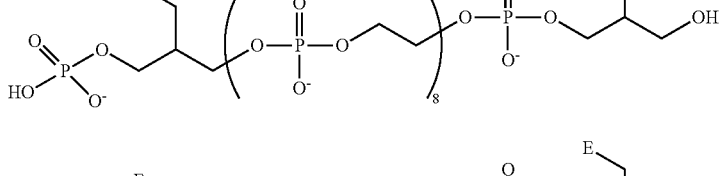 |
| EC₉E | 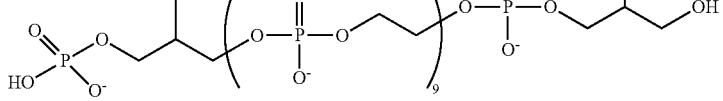 |

TABLE 2-continued

Exemplary Compounds

| Name | Structure |
|---|---|
| EC₁₀E | |
| E(C₆E)₂ | |
| E(C₇E)₂ | |
| E(C₈E)₂ | |
| E(C₉E)₂ | |
| EC₃F | |
| EC₄F | |

TABLE 2-continued

Exemplary Compounds

| Name | Structure |
|------|-----------|
| EC$_5$F | 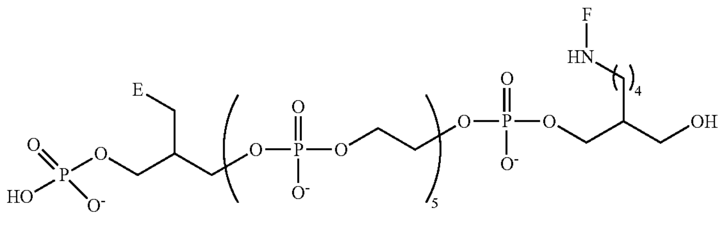 |
| EC$_6$F | 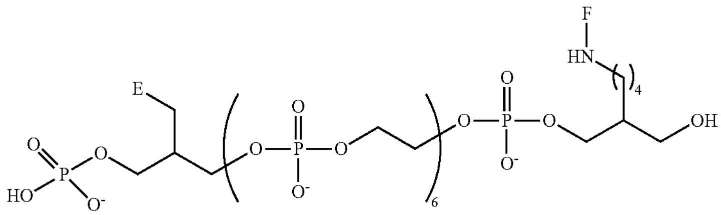 |

As used in Table 2, and throughout the application, F, E and Y refer to fluorescein, perylene and pyrene moieties, respectively, and have the following structures:

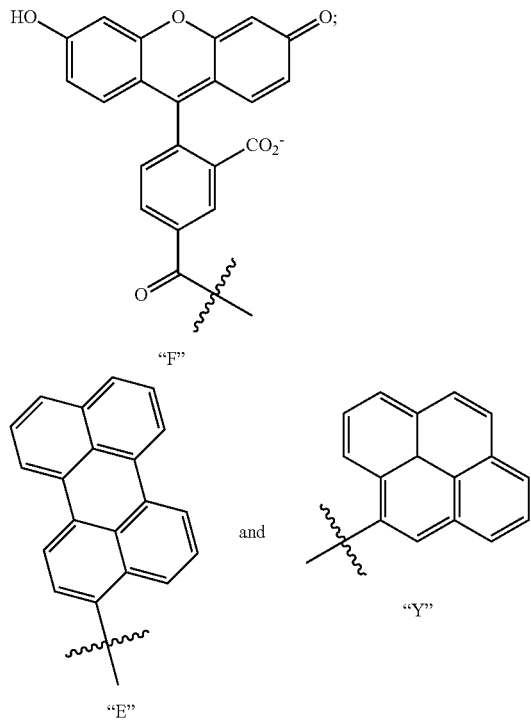

The presently disclosed dye compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of M, m, n and $L^4$ is believed to play an important role in the molar fluorescence of the compounds. Accordingly, in one embodiment is provided a method for obtaining a compound having a desired molar fluorescence, the method comprising selecting an M moiety having a known fluorescence, preparing a compound of structure (I) comprising the M, and selecting the appropriate variables for m, n and $L^4$ to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9×10× or even higher relative to the parent fluorophore. Various embodiments include preparing compounds having the desired fold increase in fluorescence relative to the parent fluorophore by proper selection of m, n and $L^4$.

For ease of illustration, various compounds comprising phosphorous moieties (e.g., phosphate and the like) are depicted in the anionic state (e.g., —OPO(OH)O⁻, —OPO$_3^{2-}$). One of skill in the art will readily understand that the charge is dependent on pH and the uncharged (e.g., protonated or salt, such as sodium or other cation) forms are also included in the scope of the invention.

Compositions comprising any of the foregoing compounds and one or more analyte molecules (e.g., biomolecules) are provided in various other embodiments. In some embodiments, use of such compositions in analytical methods for detection of the one or more analyte molecules are also provided.

In still other embodiments, the compounds are useful in various analytical methods. For example, in certain embodiments the disclosure provides a method of staining a sample, the method comprising adding to said sample a compound of structure (I), wherein one of $R^2$ or $R^3$ is a linker comprising a covalent bond to an analyte molecule (e.g., biomolecule) or microparticle, and the other of $R^2$ or $R^3$ is H, OH, phosphate or thiophosphate, in an amount sufficient to produce an optical response when said sample is illuminated at an appropriate wavelength.

In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:
(a) providing a compound of structure (I), wherein one of $R^2$ or $R^3$ is a linker comprising a covalent bond to the analyte molecule, and the other of $R^2$ or $R^3$ is H, OH, phosphate or thiophosphate; and
(b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:
(a) admixing any of the foregoing compounds with one or more analyte molecules; and
(b) detecting the compound by its visible properties.

In some other different embodiments, the compounds of structure (I) can be used in various methods for analysis of cells. For example, by use of flow cytometry, the compounds can be used to discriminate between live and dead cells, evaluate the health of cells (e.g., necrosis vs. early apoptitic vs. late apoptitic vs. live cell), tracking ploidy and mitosis during the cell cycle and determining various states of cell proliferation. While not wishing to be bound by theory, it is believed that embodiments of the compounds of structure (I) preferentially bind or associate with positively charged moieties. Accordingly, in some embodiments the compounds may be used in methods for determining the presence of non-intact cells, for example necrotic cells. For example, in some embodiments is provided a method for determining the presence of necrotic cells, the method comprising admixing a sample containing cells with a compound of structure (I) and analyzing the mixture by flow cytometry. The compound of structure (I) binds or associates with necrotic cells, and thus the presence of necrotic cells is detectable under flow cytometry conditions. In contrast to other staining reagents which require an amine reactive group (or other reactive group) to bind to necrotic cells, embodiments of the staining methods employing compounds of structure (I) do not require a protein-free incubation buffer, and thus the methods are more efficient to perform than related known methods.

Accordingly, in some embodiments the invention provides a method for determining the presence of dead cells (or non-intact cells or necrotic tissue, etc.) in a sample, the method comprising contacting the sample with a compound of structure (I), thereby binding or associating the compound with the dead cells, and observing a fluorescent signal from the compound bound or associated with the dead cells. For example, some embodiments comprise use of flow cytometry to observe the compound bound or associated with the dead cells. As noted above, certain methods do not require use of reactive groups to bind or associate with the dead cells. Accordingly, in certain embodiments the compound of structure (I) for use in identification of dead cells is a compound of structure (I), wherein $R^2$ and $R^3$ are each independently OH or —OP(=$R_a$)($R_b$)$R_c$.

In various other embodiments, the compounds can be used in related methods for determine the presence of positively charged moieties in intact or non-intact cells, apoptitic bodies, depolarized membranes and/or permealized membranes.

In addition to the above methods, embodiments of the compounds of structure (I) find utility in various disciplines and methods, including but not limited to: imaging in endoscopy procedures for identification of cancerous and other tissues; identification of necrotic tissue by preferential binding of the compounds to dead cells; single-cell and/or single molecule analytical methods, for example detection of polynucleotides with little or no amplification; cancer imaging, for example by conjugating a compound of structure (I) to an antibody or sugar or other moiety that preferentially binds cancer cells; imaging in surgical procedures; binding of histones for identification of various diseases; drug delivery, for example by replacing the M moiety in a compound of structure (I) with an active drug moiety; and/or contrast agents in dental work and other procedures, for example by preferential binding of the compound of structure (I) to various flora and/or organisms.

It is understood that any embodiment of the compounds of structure (I), as set forth above, and any specific choice set forth herein for a $R^1$, $R^2$, $R^3$, $R^4$, $R^5$, $L^1$, $L^2$, $L^3$, $L^4$, M, m and n variable in the compounds of structure (I), as set forth above, may be independently combined with other embodiments and/or variables of the compounds of structure (I) to form embodiments of the inventions not specifically set forth above. In addition, in the event that a list of choices is listed for any particular $R^1$, $R^2$, $R^3$, $R^4$, $R^5$, $L^1$, $L^2$, $L^3$, $L^4$, M, m and n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

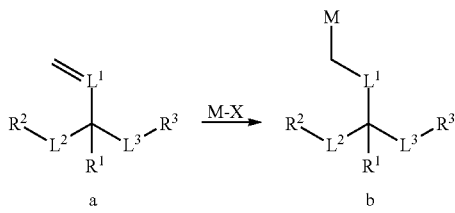

a          b

Reaction Scheme I illustrates an exemplary method for preparing an intermediate useful for preparation of compounds of structure (I), where $R^1$, $L^1$, $L^2$, $L^3$ and M are as defined above, and $R^2$ and $R^3$ are as defined above or are protected variants thereof. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of compounds of structure (I) as described below.

Reaction Scheme II

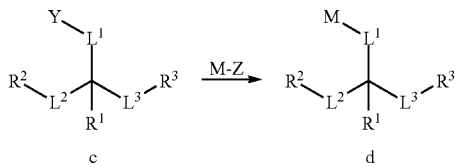

c          d

Reaction Scheme II illustrates an alternative method for preparation of compounds of intermediates useful for preparation of compounds of structure (I). Referring to reaction Scheme II, where $R^1$, $L^1$, $L^2$, $L^3$ and M are as defined above, and $R^2$ and $R^3$ are as defined above or are protected variants thereof, a compound of structure c, which can be purchased or prepared by well-known techniques, is reacted with M-Z to yield compounds of structure d. Here, Y and Z represent functional groups having complementary reactivity (i.e., functional groups which react to form a covalent bond). Z may be pendant to M or a part of the structural backbone of M, for example a cyclic anhydride. Y may be any number of functional groups, such as amino.

In certain embodiments, the compounds of structure I are oligomers comprising from 2-100 repeating units. Such oligomers can be prepared using methods analogous to well-known automated DNA synthesis methods. DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-diisopropylchlorophosphoramidite. Methods for preparation of phosphoramidites and their oligomerization are well-known in the art and described in more detail in the examples.

Oligomers of intermediates b or d are prepared according to the well-known phophoramidite chemistry described above. The desired number of m repeating units is incorporated into the molecule by repeating the phosphoramidite coupling the desired number of times with an appropriate intermediate, for example an intermediate having the following structure:

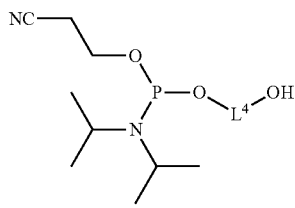

The following examples are provided for purposes of illustration, not limitation.

EXAMPLES

General Methods $^1$H and $^{31}$P NMR spectra were obtained on a JEOL 400 MHz spectrometer. $^{31}$P NMR spectra were referenced against 85% aqueous phosphoric acid and $^1$H spectra were referenced against TMS. Reverse phase HPLC dye analysis was performed using a Waters Acquity UHPLC system with a 2.1 mm×50 mm Acquity BEH-C18 column held at 45° C. Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were analyzed using an Agilent Infinity 1260 UHPLC system with a diode array detector and High Performance Autosampler using an Aapptec® Spirit™ Peptide C18 column (4.6 mm×100 mm, 5 m particle size). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic acid, pyridine, and THF were purchased from Aldrich. All other chemicals were purchased from Aldrich or TCI and were used as is with no additional purification.

All oligomer (i.e., dimer and higher) dyes were synthesized on an ABI 394 DNA synthesizer using standard protocols for the phosphoramidite-based coupling approach. The chain assembly cycle for the synthesis of oligomers was the following: (i) detritylation, 3% trichloroaceticacid in dichloromethane, 1 min; (ii) coupling, 0.1 M phosphoramidite and 0.45 M tetrazole in acetonitrile, 10 min; (iii) capping, 0.5 M acetic anhydride in THF/lutidine, 1/1, v/v 15 s; (iv) oxidation, 0.1 M iodine in THF/pyridine/water, 10/10/1, v/v/v, 30 s.

Chemical steps within the cycle were followed by acetonitrile washing and flushing with dry argon for 0.2-0.4 min. Cleavage from the support and removal of base and phosphoramidate protecting groups was achieved by treatment with ammonia for 1 hour at room temperature. Oligomer dyes were then analyzed by reverse phase HPLC as described above.

Example 1

Synthesis of Phosphoramidite Dye Monomers

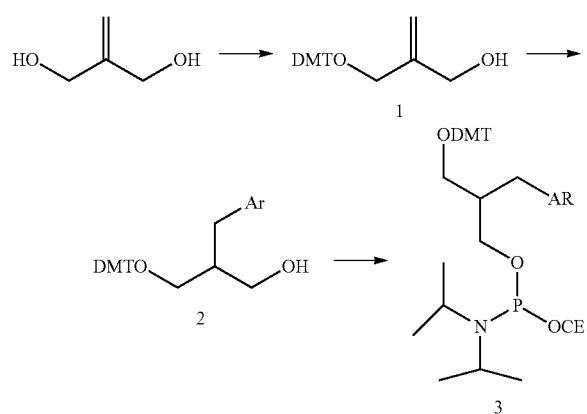

Ar = pyrene
DMT = 4,4'-dimethoxytrityl
CE = 2-cyanoethyl

1-O-(4,4'-dimethoxytrityl-2-methylene-1,3-propanediol(1)

Into a dry 500 mL round bottom flask was put a stir bar. After flushing with nitrogen, dry pyridine (240 mL) was added, and the flask was cooled in an ice bath for 15 minutes. Upon cooling DMTrCl (7.65 g, 22.5 mmol) was added after which the flask was stirred overnight in a refrigerator at 4° C. under a nitrogen atmosphere. Several drops of methanol were then added and the reaction was concentrated in vacuo to a viscous gum. The resulting gum was dissolved in EtOAc (200 mL) and washed with $NaHCO_3$ (250 mL) and sat. NaCl (250 mL). The organic layer was dried over $Na_2SO_4$ and concentrated in vacuo to a viscous gum. The isolated crude product wash then purified by silica gel column chromatography eluting with a gradient of EtOAc:hexanes (25:75 v/v)-(1:1 v/v) to give 1 as a clear gum (5.21 g, 60%). $^1H$ NMR was recorded and found to be consistent with the structure of compound 1.

1-O-(4,4'-dimethoxytrityl)-2-hydroxymethyl-3-pyrenylpropanol(2)

Into a dry 250 mL round bottom flask fitted with a condenser was put a stir bar. The flask was purged with nitrogen, and dry THF (40 mL) and compound 1 (5.0 g, 12.8 mmol) were added. 0.5 M 9-BBN in THF (65 mL, 32 mmol) was added via syringe and the reaction was heated to reflux for 12 hrs. After allowing the reaction to cool to room temperature, 3M $K_2CO_3$ (11 ml) and dry DMF (100 mL) were added. 1-Bromopyrene (2.0 g, 6.5 mmol) and $PdCl_2$ (dppf) (0.65 g, 0.8 mmol) were added, and the solution was allowed to stir for 15 hrs at room temperature. The reaction mixture was poured into $CH_2Cl_2$ (300 mL) and washed with $H_2O$ (500 mL). The aqueous layer was then back extracted with additional $CH_2Cl_2$ (200 mL). The combined organic layers were washed with sat. NaCl (300 mL), dried over $Na_2SO_4$, and concentrated in vacuo to a viscous gum. The isolated crude product wash then purified by silica gel column chromatography eluting with a gradient of EtOAc:hexanes (25:75 v/v)-(1:1 v/v) to give 2 as a clear gum (3.0 g, 79%). The $^1H$ NMR spectrum was recorded and found to be consistent with the structure of compound 2.

1-O-(4,4'-dimethoxytrityl)-2-methylpyrene-3-O-(2-cyanoethyl-N,N-diisopropyl) propane phosphoramidite (3)

Into a dry 100 mL round bottom flask was put a stir bar. After purging the flask with nitrogen, $CH_2Cl_2$ (20 mL) and compound 2 (0.30 g, 0.50 mmol) were added. N,N-Diisopropylethylamine (0.88 mL, 5.0 mmol) and 2-cyanoethyl diisopropychlorophosphoramidite (0.45 mL, 2.0 mmol) were added via syringe. After 1 hour of stirring at room temperature, the reaction was determined to be complete by TLC analysis. The crude reaction mixture was then purified directly by silica gel column chromatography eluting with a gradient of EtOAc:hexanes:TEA (22.5:72.5:5 v/v/v) to give 3 as a white foam (0.28 g, 70%). The $^{31}P$ NMR spectrum was recorded and found to be consisted with the structure of compound 3: Purity was determined by HPLC analysis with detection at 254 and 340 nm.

Other compounds with different Ar groups (e.g., any of the "M" groups described herein) were prepared in an analogous manner.

Example 2

Synthesis of Perylene Carbodiimide Dye Monomer

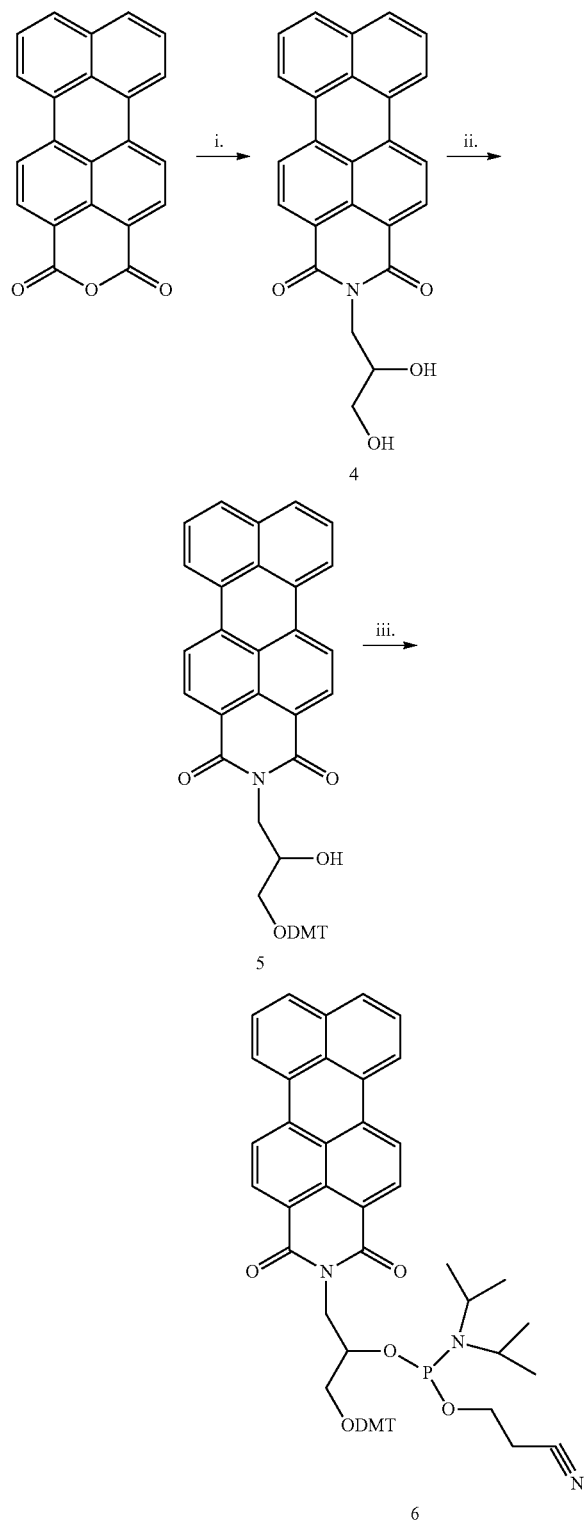

N-(2,3-propanediol) perylenemonoimide(4)

Into a dry 200 mL round bottom flask fitted with a condenser was put a stir bar and perylene monoanhydride[1] (1.83 g, 5.67 mmol). After adding 3-amino-1,2-propanediol (1.1 g, 2.1 mmol) and imidazole (14.3 g, 0.21 mol), the vessel was heated to 140° C. in an oil bath for 15 hours. The reaction was allowed to cool to room temperature and then 10% HCl was added (500 mL). The resulting deep red precipitate was collected by filtration, washed well with water and dried at 180° C. for several hours to yield 4 as a deep red solid (1.95 g, 86%).

N-(3-O-(4,4'-dimethoxytrityl-2-hydroxypropane) perylenemonoimide(5)

Into a dry 200 mL round bottom flask was put a stir bar. After purging the flask with nitrogen, dry pyridine (120 mL), compound 4 (0.44 g, 1.1 mmol), and dimethoxytritylchloride (0.45 g, 1.3 mmol) were all added, and the reaction was allowed to stir at room temperature for 48 hours. Several drops of methanol were then added, and the reaction was concentrated in vacuo to a viscous gum. The resulting gum was dissolved in $CH_2Cl_2$ (200 mL) and washed with sat. NaCl (200 mL). The aqueous layer was washed with in $CH_2Cl_2$ (3×100 mL). The combined organic layers were dried over $Na_2SO_4$ and concentrated in vacuo to a viscous gum. The isolated crude product wash then purified by silica gel column chromatography eluting with a gradient of EtOAc: $CH_2Cl_2$ (0:100 v/v)-(2:3 v/v) to give 5 as a red foam (0.25 g, 50%).

N-(3-O-(4,4'-dimethoxytrityl-2-O-(2-cyanoethyl-N, N-diisopropylamide phosphoramidite) perylenemonoimide (6)

Into a dry 50 ma round bottom flask was put a stir bar. After purging the flask with nitrogen, $CH_2Cl_2$ (5 mL) and compound 5 (0.25 g, 0.36 mmol) were added. N,N-diisopropylethylamine (0.24 mL, 1.79 mmol) and 2-cyanoethyl N,N-diisopropychlorophosphoramidite (0.16 mL, 0.72 mmol) were added via syringe. After 1 hour of stirring at room temperature, the reaction was determined to be complete by TLC analysis. The crude reaction mixture was then purified directly by silica gel column chromatography eluting with $CH_2Cl_2$:TEA (95:5 v/v) to give 6 as a dark red foam (0.26 g, 80%). The purified compound was analyzed by RP-HPLC with observation at 254 and 500 nm. Two diastereomers were found to be present.

Other dye monomers with different M groups were prepared in an analogous manner.

Example 3

Synthesis of Oligomer Dyes

Oligomer dyes were synthesized on an Applied Biosystems 394 DNA/RNA synthesizer or on GE AKTÄ 10 OligoPilot on either 1 μmol or 10 μmol scales and possessed a 3'-phosphate group. Dyes were synthesized directly on CPG beads or on polystyrene solid support. The dyes were synthesized in the 3' to 5' direction by standard solid phase DNA methods. Coupling methods employed standard 3-cyanoethyl phosphoramidite chemistry conditions. Different number of "m" repeating units were incorporated by repeating the synthesis cycle the desired number of times with an appropriate phosphoramidite. All phosphoramidite monomers were dissolved in acetonitrile/dichloromethane (0.1 M solutions), and were added in successive order using the following synthesis cycles: 1) removal of the 5'-dimethoxytrityl protecting group with dichloroacetic acid in toluene, 2) coupling of the next phosphoramidite with activator reagent in acetonitrile, 3) oxidation with iodine/pyridine/water, and 4) capping with acetic anhydride/1-methylimidizole/acetonitrile. The synthesis cycle was repeated until the 5' Oligofloroside was assembled. At the end of the chain assembly, the monomethoxytrityl (MMT) group or dimthoxytrityl (DMT) group was removed with dichloroacetic acid in dichloromethane or dichloroacetic acid in toluene.

The dyes were cleaved from the solid support and deprotected as follows:

A 1 mL micropipettor was used to add 450 µL of concentrated $NH_4OH$ to ~25 mg of reacted CPG solid support in a 1.5 mL Eppendorf tube. The slurry was mixed briefly using a Vortex mixer and allowed to settle before placing (open) on a 55° C. heating block until gas formation (and bubbling) started to diminish, at which point the tube was tightly closed. Heat treatment was for 2 hours (+/−15 minutes) and tubes were then removed to cool to room temperature. The tube and its contents were spun in a centrifuge at its maximum speed (13400 rpm) for 1 minute, and then the supernatant was removed with a glass pipette and placed into a second, labeled, 1.5 mL Eppendorf tube, taking care not to include the support. The support was washed and spun-down 2× with ~150 µL of acetonitrile to help maximize dye removal, and the washings were carefully removed from support and added to the labeled secondary tubes. Clarified supernatant was dried completely in a CentriVap concentrator at 40° C. to remove $NH_4OH$.

Example 4

Characterization of Oligomer Dyes 1 mL of deionized water was added to the dried dye sequence prepared according to Example 3 to re-constitute and establish a concentrated stock of ~0.3 to 1.0 mM (determined later). 2 µL aliquots of each dye construct were analyzed by HPLC-MS to determine identity and relative purity using 45° C. heated ultra-high performance 2.1 mm×50 mm C18 column (1.7 µm) with 150 mM HFIP/TEA (pH9) mobile phase, and methanol as organic elution component. Gradient was from 1-100% over 10 minutes. Electrospray ionization was used (in negative mode) to determine the molecular weights of the dye sequences and help to characterize impurities.

A sample was taken from a concentrated stock using a micropipettor and diluted appropriately in 0.1×PBS (10× to 100×) to be within linear range of the NanoDrop UV-vis spetrophotomer (Thermo Scientific). A blank measurement was performed on the NanoDrop using 0.1×PBS, and then the absorbance of the diluted dye sequence at an appropriate wavelength was recorded. Extinction coefficients (E) were determined by the total number of fluors (M moieties) in the dye construct, using 75,000 $M^{-1}$ $cm^1$ for each fluorescein (F; read at 494 nm); 34,500 for each pyrene (Y; read at 343 nm); and 40,000 for each perylene (E; read at 440 nm) present in the sequence. Spacers are presumed to have no effect on ε. An exemplary calculation of the molar concentration of a dye having the structure $[F(CCCCCCCF)_5]$ is as follows:

$$\text{Molar concentration of dye} = \{A_{494}/(L^* \varepsilon_{Dye})\}^* \text{Dilution Factor} \qquad \text{Equation 1:}$$

$E_{Dye}$=450,000 $M^{-1}$ $cm^{-1}$ $L_{nanodrop}$=0.1 cm $A_{494}$=0.254 AU

Dilution Factor=100

Molar concentration of Dye=5.64×$10^{-04}$ M, or 0.564 mM.

With concentration determined, the dye stock was diluted in the $NaPO^4$ (0.1 µM at pH 7.5) and $NaCO^3$ (0.1 M at pH 9.0) buffers to make solutions of 2 µM (or 5 µM, whatever works with the linear range of the instrument) at a final volume of ~3.5 mL. These solutions were scanned by UV/Vis, and then used them to make a second dilution in the appropriate buffer for reading on the fluorimeter, in the range of 10-50 nM. The necessary concentration will vary depending upon the identity of the M moiety. For the above dye, a 25 nM solution was used Using a 1 cm quartz cuvette, the absorbance of the 2 µM sample was determined, scanning from 300 nm to 700 nm. Scan speed was set to medium.

Using a 1 cm quartz cuvette and a Cary Eclipse spectrometer, the emission of the 25 nM sample was read using an appropriate excitation wavelength (494 nm for above dye) and scanning from 499 nm to 700 nm. Scan speed was set to medium.

Example 5

UV and Fluorescence Properties of Oligomer Dyes

The dye compounds listed in Table 3 were prepared according to the above general procedures and their UV and fluorescence properties were determined at 2 nM and pH 9. As can be seen from the UV spectra in FIG. 1, the extinction coefficients of the various dye compounds roughly correspond to the theoretical value (i.e., the extinction coefficients are additive).

Figure 2:
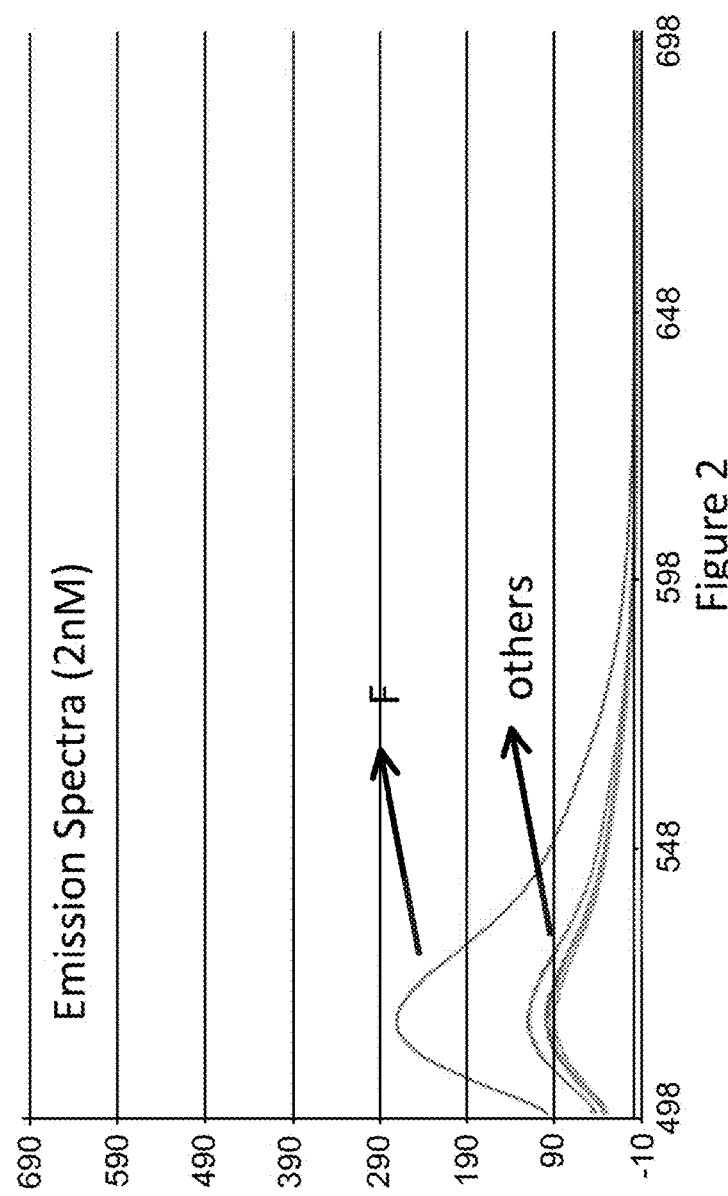
FIG. 2 is an overlay of fluorescent emission spectra for comparative dye compounds.

The fluorescence emission spectra from 499 nm to 700 nm of the dyes in Table 3 was also determined (FIG. 2). In contrast to the extinction coefficients, the emission of the dyes containing multiple fluorescent moieties was significantly less than the parent compound (F). While not wishing to be bound by theory, it is believed that this phenomenon can be explained by intramolecular quenching of fluorescence by the multiple fluorescent moieties.

TABLE 3

| Name | Structure | $\epsilon_t$* |
|---|---|---|
| F | F—OH | 75k |
| FCF | (structure) | 150k |
| F(CF)$_2$ | (structure) | 225k |
| F(CF)$_3$ | (structure) | 300k |
| F(CF)$_4$ | (structure) | 375k |
| F(CF)$_5$ | (structure) | 450k |
| F(CF)$_6$ | (structure) | 525k |

$\epsilon_t$ = theoretical molar extinction coefficient

Example 6

UV and Fluorescence Properties of Oligomer Dyes

To explore the effects of various linker lengths between the fluorescent moieties, the dye compounds listed in Table 4 were prepared according to the above general procedures and their UV and fluorescent properties determined.

Figure 3:
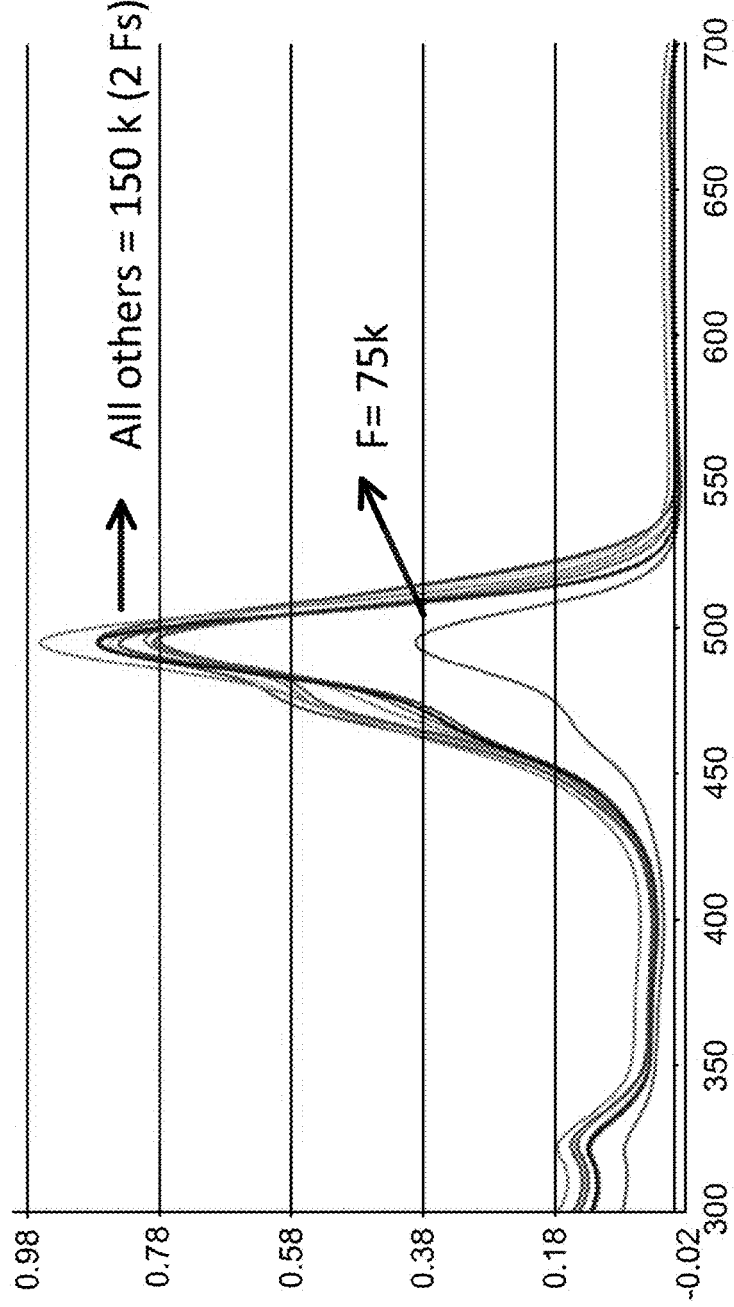
FIG. 3 presents UV absorption spectra for exemplary dye compounds.
Figure 4:
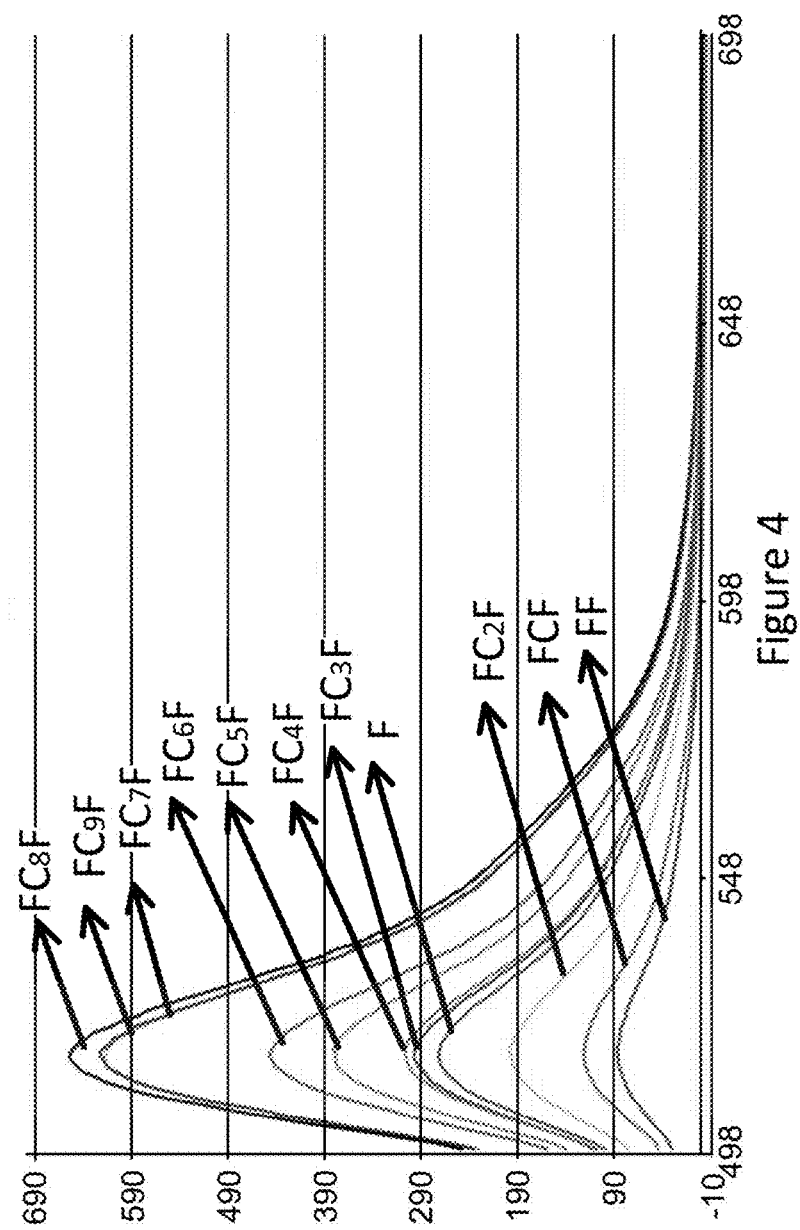
FIG. 4 shows fluorescent emission spectra for the dye compounds of FIG. 3.

The extinction coefficients of each of the fluorescein dimer dyes in Table 4 roughly corresponds with the expected theoretical value based on the sum of the two fluorescein moieties (FIG. 3). Surprisingly, the fluorescent emission spectra of the dimers indicate that the linker length has a significant effect on the fluorescent emission of the dye (FIG. 4). Specifically, it was found that inclusion of at least "C" spacers (see structure below) between the fluorescein moieties resulted in an overall increase in emission relative to a single fluorescein, whereas shorter linkers between the fluorescein moieties resulted in decreased fluorescence relative to a single fluorescein.

TABLE 4

| | Dye Compounds | |
|---|---|---|
| Name | Structure | $\epsilon_t^*$ |
| F | F—OH | 75k |
| FF | [structure] | 150k |
| FCF | [structure] | 150k |
| FC$_2$F | [structure] | 150k |
| FC$_3$F | [structure] | 150k |
| FC$_4$F | [structure] | 150k |

TABLE 4-continued

Dye Compounds

| Name | Structure | $\epsilon_t^*$ |
|---|---|---|
| $FC_5F$ | 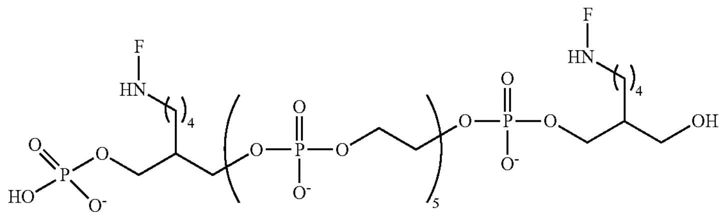 | 150k |
| $FC_6F$ | 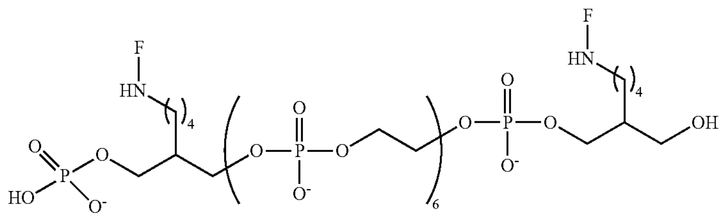 | 150k |
| $FC_7F$ | 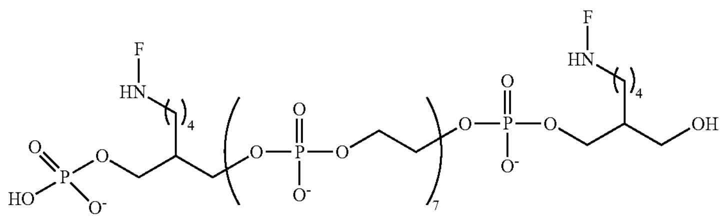 | 150k |
| $FC_8F$ | 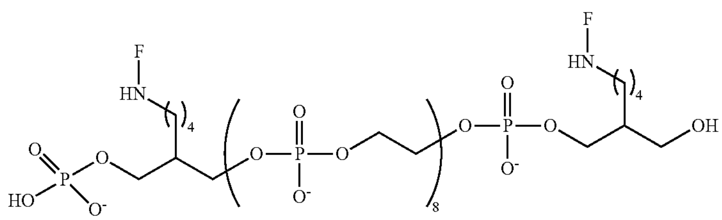 | 150k |
| $FC_9F$ | 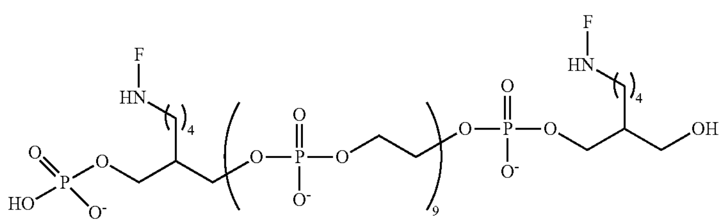 | 150k |

$\epsilon_t$ and F are as defined above, and the "C linker" has the following structure:

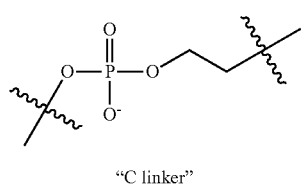

"C linker"

Example 7

UV and Fluorescence Properties of Oligomer Dyes

To explore the effects of the number of fluorescent moieties within a dye molecule, the dye compounds listed in Table 5 were prepared according to the above general procedures and their UV and fluorescent properties determined at 2 nM and pH 9.

Figure 5:
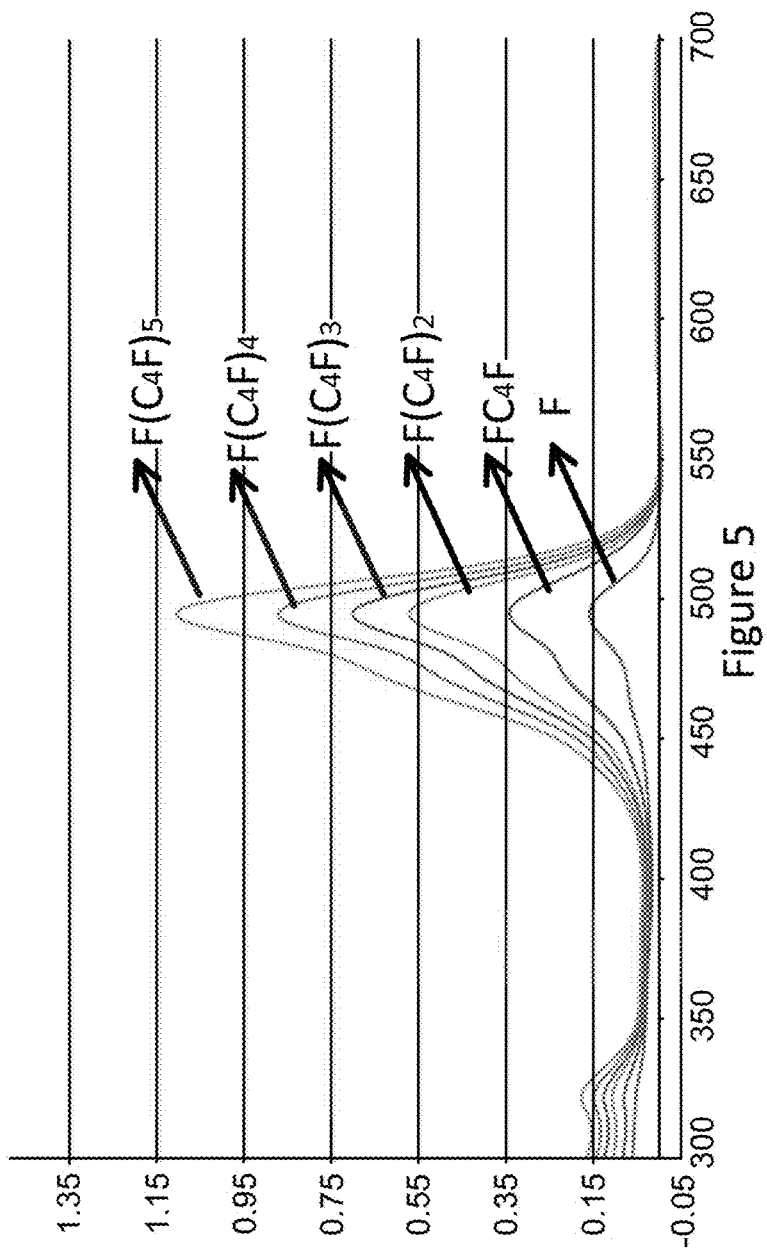
FIG. 5 is another overlay of UV absorption spectra of representative dye compounds.
Figure 6:
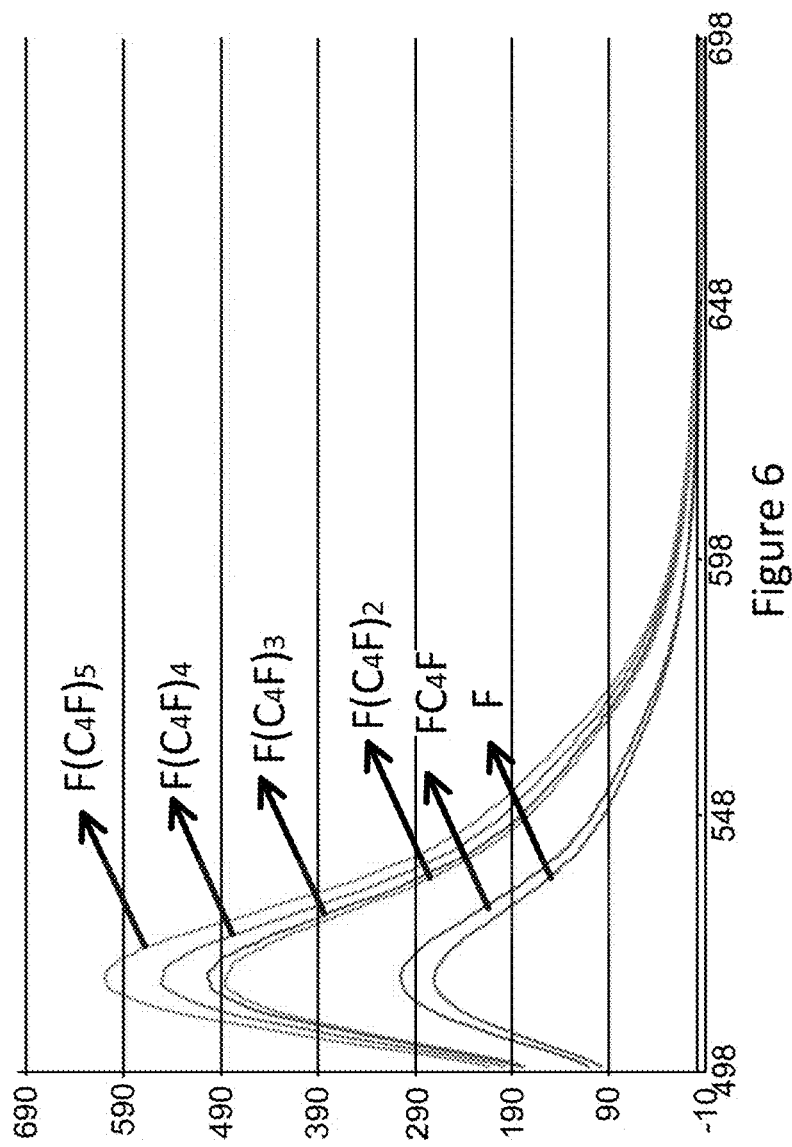
FIG. 6 illustrates fluorescent emission spectra for representative dye compounds.

Again the extinction coefficients of each of the fluorescein dimer dyes in Table 5 was additive and roughly corresponds with the expected theoretical value (FIG. 5). The fluorescent emission of each of the compounds in Table 5 is brighter than the parent (i.e., monomer) fluorophore (FIG. 6).

TABLE 5

Dye Compounds

| Name | Structure | $\epsilon_t$* |
|---|---|---|
| F | F—OH | 75k |
| FC$_4$F | [structure] | 150k |
| F(C$_4$F)$_2$ | [structure] | 225k |
| F(C$_4$F)$_3$ | [structure] | 300k |
| F(C$_4$F)$_4$ | [structure] | 375k |
| F(C$_4$F)$_5$ | [structure] | 450k |

$\epsilon_t$ and F are as defined above.

Example 8

UV and Fluorescence Properties of Oligomer Dyes

The dye compounds listed in Table 6 were prepared according to the above general procedures and their fluorescent emission properties determined at 25 nM and pH 9.

Figure 7:
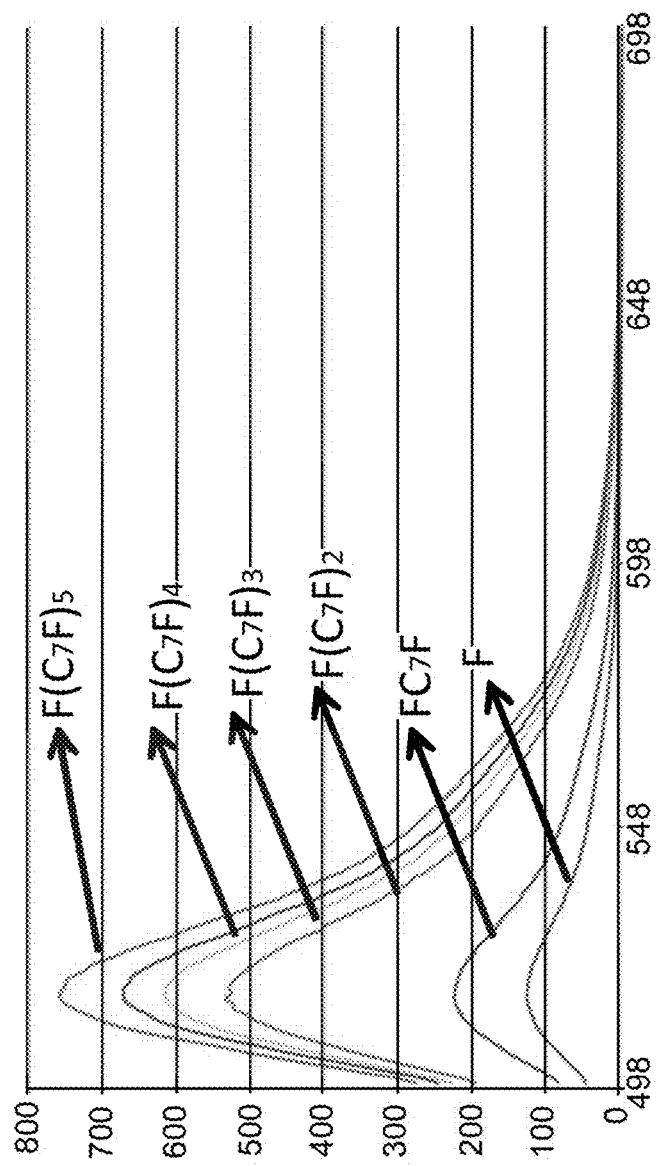
FIG. 7 provides another overlay of fluorescent emission spectra for representative dye compounds relative to the parent fluorophore.

The fluorescent emission spectra indicate that each of these compounds are brighter than the parent (i.e., monomer) fluorophore, with one compound being approximately 6× brighter (FIG. 7).

TABLE 6

Dye Compounds

| Name | Structure | $\epsilon_t^*$ |
|---|---|---|
| F | F—OH | 75k |
| $FC_7F$ | [structure] | 150k |
| $F(C_7F)_2$ | [structure] | 225k |
| $F(C_7F)_3$ | [structure] | 300k |
| $F(C_7F)_4$ | [structure] | 375k |
| $F(C_7F)_5$ | [structure] | 450k |

$\epsilon_t$ and F are as defined above.

Example 9

UV and Fluorescence Properties of Oligomer Dyes

The compounds in Table 7 were prepared according to the above general procedures and their fluorescent emission properties determined at 10 nM and pH 9.

Figure 8:
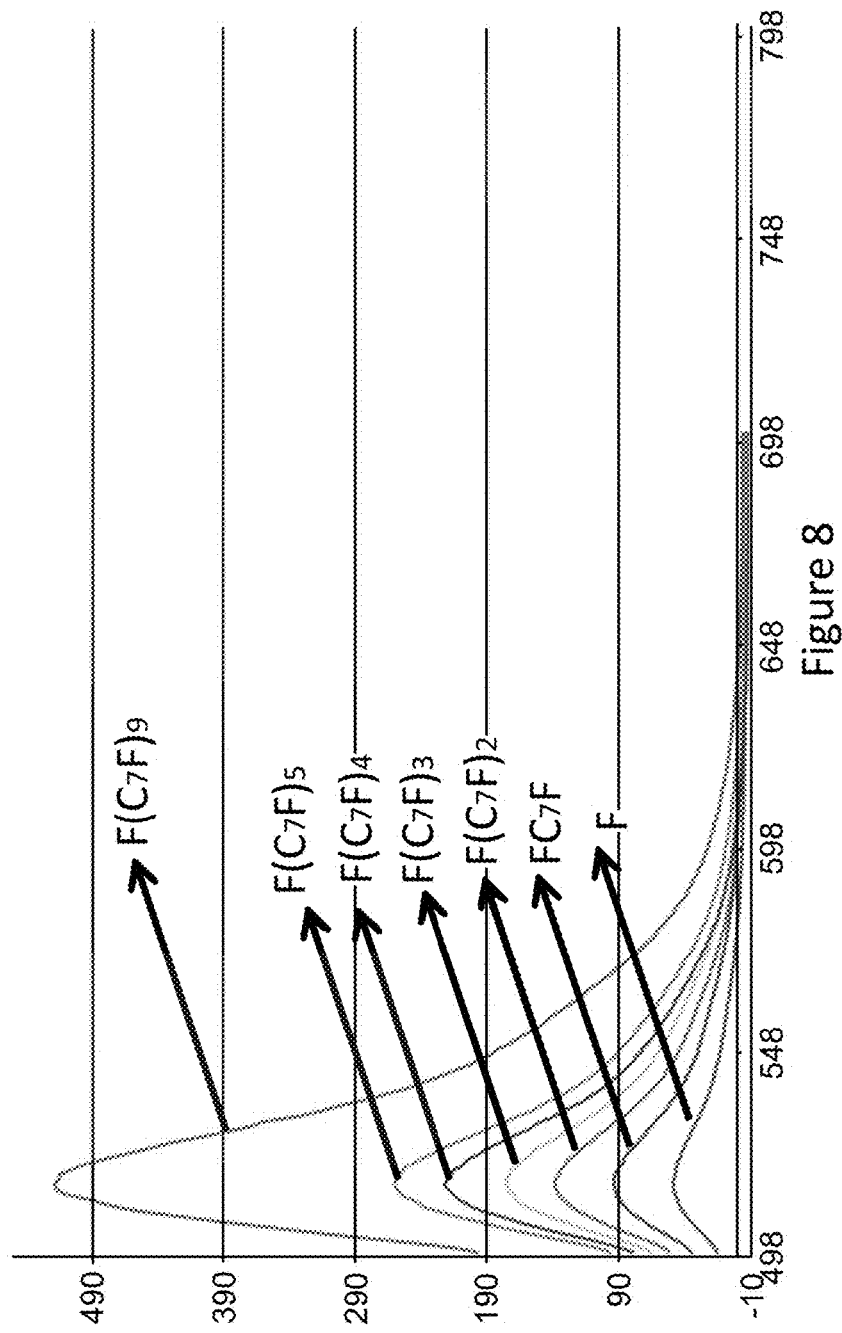
FIG. 8 is another overlay of fluorescent emission spectra for representative dye compounds relative to the parent fluorophore.

The fluorescent emission spectra of these compounds again show that these compounds are brighter than the parent (i.e., F) fluorophore (FIG. 8, unity value not shown).

TABLE 7

Dye Compounds

| Name | Structure |
|---|---|
| F | F—OH |
| FC$_7$F | (structure) |
| F(C$_7$F)$_2$ | (structure) |
| F(C$_7$F)$_3$ | (structure) |
| F(C$_7$F)$_4$ | (structure) |
| F(C$_7$F)$_5$ | (structure) |
| F(C$_7$F)$_9$ | (structure) |

F is as defined above.

Example 10

UV and Fluorescence Properties of Oligomer Dyes Containing Perylene

Dye compounds comprising a perylene moiety ("E") were prepared according to the above general procedures and their fluorescent emission properties determined at 50 nM and pH 9. The structure of these dyes is presented in Table 8.

The fluorescent emission spectra indicate that each of these compounds are brighter than the parent (i.e., "unity") fluorophore (FIG. 9). The ability to use perylene in an aqueous environment, and increase its brightness on a molar basis, is a major advance given the hydrophobic nature of this fluorophore.

TABLE 8

Perylene Containing Dye Compounds

| Name | Structure |
|---|---|
| E | (structure shown) |
| E(C$_6$E)$_2$ | (structure shown) |
| E(C$_7$E)$_2$ | (structure shown) |

E is as defined above.

Example 11

General Flow Cytometry Method and Applications

The general flow cytometry workflow includes the following steps:
1. Culture and visually observe cells for signs of metabolic stress and/or use fresh, induced, or simulated cells.
2. Dilute dye compounds to working volumes.
3. Harvest and prepare cells without killing or inducing apoptosis.
4. Centrifuge and wash cells with appropriate buffer.
5. Perform cell counts using hemocytometer and trypan blue exclusion.
6. Centrifuge and wash cells
7. Adjust cell density to test size
8. Apply dye (pre-dilution) or other co-stains of interest.
9. Incubate the cell/stain/dye mixture.
10. Centrifuge and wash cells with appropriate buffer.
11. Re-suspend cells in acquisition buffer.
12. Acquire cell data by flow cytometry.

The general workflow described above can be modified according to specific applications. Some modifications for specific applications are described below.

Live/Dead Discrimination

Cells are tested for viability by positively staining necrotic cells to compare damaged cells to intact cells. Assays are used to target non-intact (fixed and non-fixed) cells with positively charged moieties, cell debris, apoptotic bodies, depolarized cell membrane, and permeabilized membranes. Cells are then stained with dye using routine cell preparations (fresh or fixed) and analyzed using flow cytometry.

Cell Health

A comparison is made between dead cells (i.e., necrotic cells), early apoptotic, late apoptotic, and live cells. Dead cells are positively stained, Apoprotic bodies are intermediately stained, and live cells are left negative. This strategy results in very bright necrotic cells and works also to assess cell permeability. Assays are used to target non-intact (fixed and non-fixed) cells with positively charged moieties, cell debris, apoptotic bodies, depolarized cell membrane, and permeabilized membranes. Dye staining is performed on in vitro cultures, primary cells, and samples treated with xenobiotics and analyzed using flow cytometry.

Cell Cycle

Cell ploidy and mitosis in the cell cycle is tracked by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with other dyes) is performed on in vitro cultures, primary cells, and samples treated with xenobiotics and analyzed using flow cytometry.

Proliferation

Cell proliferation is monitored by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with monitoring markers for cell proliferation, e.g. Ki67, BRDU) is performed on in vitro cultures, primary cells, and samples treated with xenobiotics and analyzed using flow cytometry.

Example 12

Cell Culture of Jurkat Cells

Jurkat cells (Clone E6-1; ATCC® TIB-152™) are human lymphocyte cells found in peripheral blood tissue and used to model acute T cell Leukemia. Cells were cultured in RPMI-1640 Medium, fetal bovine serum 10%, 0.1 M HEPES, PenStrep and L-glutamine.

Cultures were maintained by addition of fresh medium or replacement of medium between $1\times10^5$ viable cells/mL and $5\times10^6$ cells/mL. Alternatively, cultures were established by centrifugation with subsequent resuspension at $1\times10^5$ viable cells/mL. Fresh medium was added every 2 to 3 days depending on cell density.

Example 13

Cell Culture of Ramos Cells

Ramos (RA 1; ATCC CRL-1596) are human B lymphocytes and are used to model Burkitt's Lymphoma (American). Cells were cultured in RPMI-1640 Medium with heat-inactivated fetal bovine serum 10%, 0.1 HEPES, PenStrep and L-glutamine.

Cultures were maintained by addition of fresh medium or replacement of medium between $1\times10^5$ viable cells/mL and $5\times10^6$ cells/mL. Alternatively, cultures were established by centrifugation with subsequent resuspension at $1\times10^5$ viable cells/mL. Fresh medium was added every 2 to 3 days depending on cell density.

Example 14

General Procedure for Inducing Cell Death and Recovering Dead Cells

Cultured cells were induced into necrosis and apoptosis in vitro to form dead cells, cell debris, and apoptotic bodies. Cells were induced by introducing heat stress and/or metabolic stress. Heat stress was performed by subjecting cultures to 57-60° C. for 3-5 minutes and then transferring cell cultures to ice for 10 minutes. Metabolic stress was performed by post log phase growth crowding, toxin, or xenobiotic treatment (e.g. 10 nM maptothecin). Fresh cells were maintained by subjecting cultures to no treatment.

Cell preparations were re-suspended in staining buffer, and then mixed in ratios to target a viable population of intact cells between 60-80% (i.e., 20-40% non-intact cellular debris-like events as measured by morphology using flow cytometry parameters FSC v. SSC). Cell viability was verified microscopically by Live/Dead trypan blue exclusion or by 7-aminoactinomycin D (7-AAD) by flow cytometry. In some experiments, mixtures of induced/non-induced cells were unnecessary. Instead, a post-log phase growth culture undergoing metabolic stress containing 30-40% necrotic and apoptotic cells was used.

Example 15

Inducing Cell Death and Recovery of Dead Cells for Jurkat and Ramos Cells

Mid-log phase Jurkat and Ramos or primary PBMC cells were induced into necrosis in vitro in order to form dead cells and cell debris. Cells were induced by heat stress by subjecting cultured cells first to 58° C. for 3-5 minutes, then transferring them to ice for 10-15 minutes. Fresh cells were maintained by subjecting cultures to no treatment.

Cells were resuspended in 1×DBS with $Ca^{++}/Mg^{++}$ at a cell density of $10\times10^6$ cells/mL. Fresh cells (~8% necrotic) and stressed cells (~20% necrotic) were then mixed in the following ratios to produce a measurable gradient of viable to necrotic cells:
1. 100% live:0% dead
2. 50% live:50% dead
3. 25% live:75% dead
4. 12.75% live:85.25% dead
5. 6% live:94% dead The expected viability ranged from 8-30%. Starting and ending viabilities were verified by 7-Aminoactinomycin D (7-AAD) by flow cytometry or typan clue exclusion.

Example 16

Reaction of Dead, Necrotic, and Apoptotic Cells with $F(C_{10}F)_9$ and $F(C_{10}F)_9SH$ Dyes Cells and dye (e.g., bulk $F(C_{10}F)_9$ or HNSA activated, amine reactive $F(C_{10}F)_9SH$, see Table 2) were reacted together in 96 well U-bottom polypropylene plates. Dyes were diluted serially in pure deionized water or sterile filtered phosphate buffered solution to a concentration range of 15,000-0.001 µM in volumes of 25-200 µL. Phosphate buffered saline was used for amine reactive dye (i.e. $F(C_{10}F)_9SH$). The dye solutions were then applied to cell preparations. Dyes diluted in water were limited to test volumes of ≤25 µL as applied to cells. Cell density was maintained at $2-3\times10^6$ cells/mL per test well ($V_{f\ range}$=100-200 µL stain buffer containing protein and metabolic inhibitors or phosphate buffered saline).

Prior to incubation with the dyes, cells were bulk washed (15-50 mL conical tubes) two or more times in complete growth medium (first wash), and wash buffer containing protein, phosphate buffered saline, and metabolic inhibitors in ratios of $2-3\times10^5$ cells/test per mL of wash (later washes). Large wash volume centrifuged (g×500) for 10 minutes. When $F(C_{10}F)_9SH$ was used, cells were resuspended in phosphate buffered saline before being stained with dye.

The dye mixtures were then incubated for 30-40 minutes at 23-25° C. After incubation, cells were washed twice with buffer (containing protein, phosphate buffered saline, and metabolic inhibitors) by the addition of 600-800 L/well. Mixtures were then centrifuged (g×350) for 5 minutes.

Figures 10A, 10B:
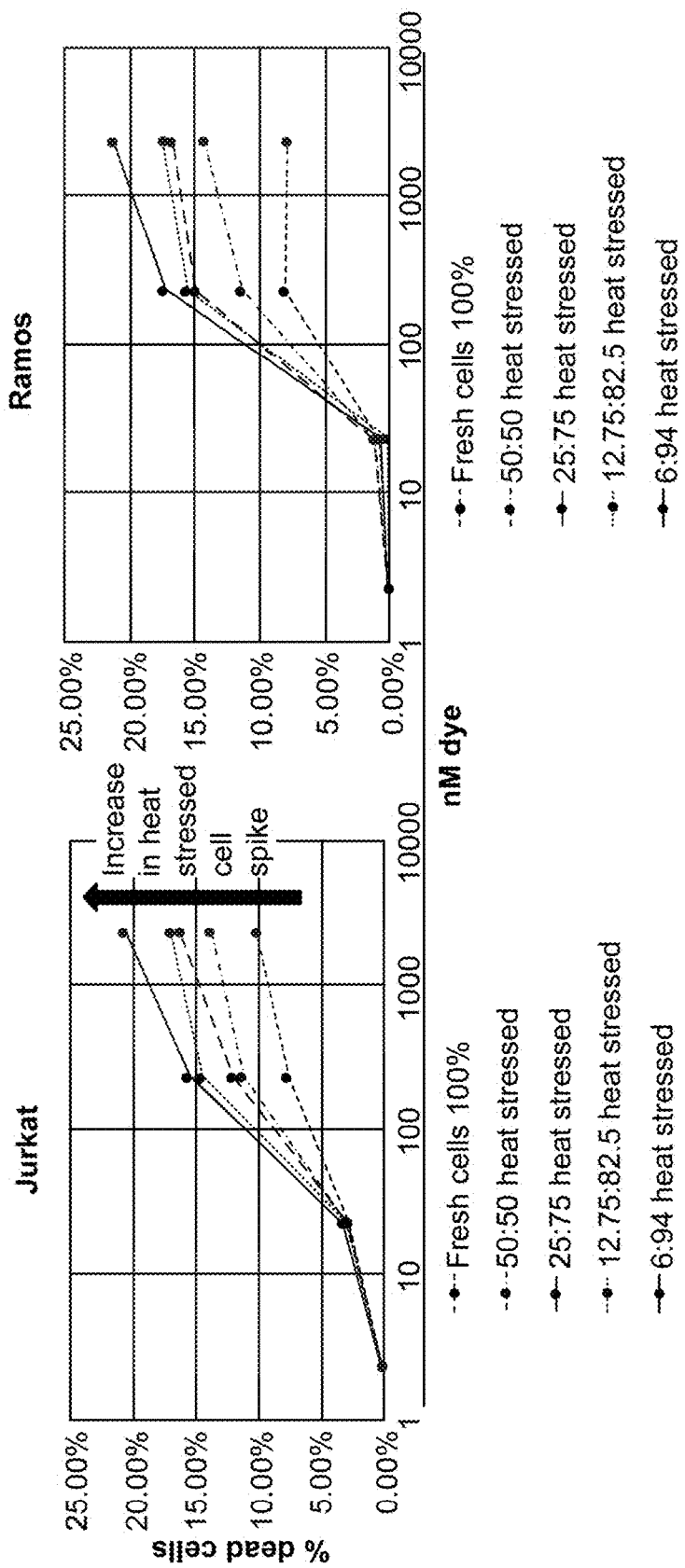
FIGS. 10a and 10b provides dose dependent data from a spike and recovery assay of cells.

The data in FIGS. 10a and 10b show that staining of necrotic cells is dose dependent with respect to the concentration of dye (e.g., $F(C_{10}F)_9SH$ or $F(C_{10}F)_9$) used.

Example 17

F(C$_{10}$F)$_9$ Staining of Cellular Material in Cell Health Evaluation

Lymphoid cancer cell lines were prepared in complete growth medium or by isolation from primary tissue and/or blood samples by density gradients, magnetic cell sorting, or FACS. Cells were then induced, in vitro, into necrosis and apoptosis to form dead cells, cell debris, and apoptotic bodies by heat or metabolic stress (see Example 14 for stress parameters). Fresh cells were maintained by no inducement.

Cells were then centrifuged and washed using standard flow cytometry wash techniques or washed with staining buffers containing protein, phosphate buffered saline, and metabolic inhibitors. F(C$_{10}$F)$_9$ dye solution was then incubated at 50 M with 0.5 mL of cells at a cell density of 2-3×10$^6$ cells/mL per test well of stain buffer. The mixtures were incubated at 20-25° C. for 30-40 minutes. After incubation, cells were washed in 600-800 µL of wash buffer (described in Example 16) and centrifuged (g×350) for 5 minutes.

DNA intercalating agents 7-aminoactinomycin D (7-AAD) viability stain and propidium iodide (PO-PRO®-1) were used together to identify necrotic and apoptotic cells in a multi-color, 5 parameter assay. Cells were centrifuged and washed to remove excess dye using standard flow cytometry wash techniques or washed with staining buffers containing protein, phosphate buffered saline, and metabolic inhibitors.

Cells were acquired by flow cytometry and analyzed to identify viable cells, early apoptotic, and late apoptotic bodies present in the cell preparation. This was achieved by targeting 5000 intact viable cells and keeping FSC-Lin threshold low enough to measure subcellular debris. Fluorescence detection was performed at 488 nM blue laser line by flow cytometry with peak emission (521 nM) detected using 525/50 bandpass filter.

Figure 11:
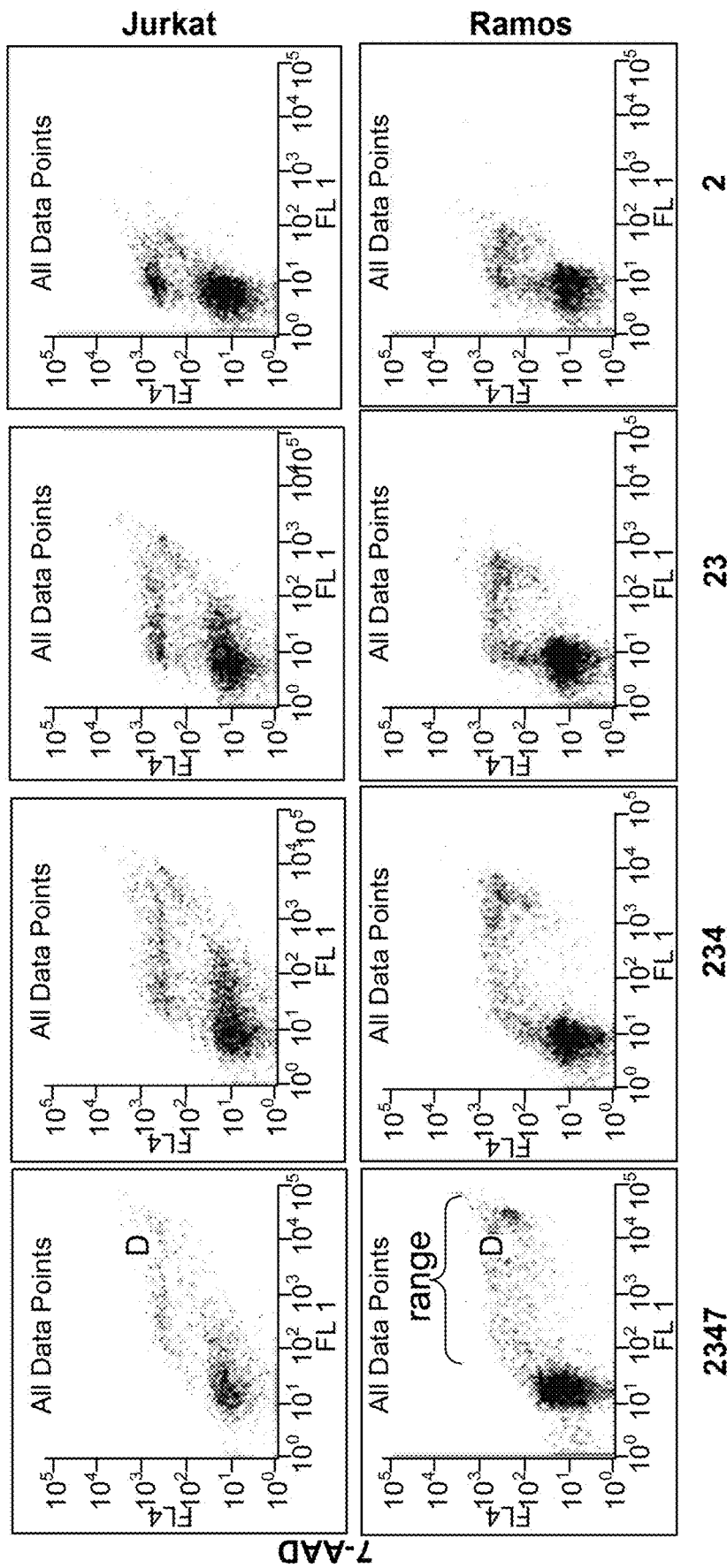
FIG. 11 provides flow cytometry data correlating live/dead gating of dye stained cells using DNA intercalated 7-AAD.

When compared to fresh cultures, the staining patterns of this cell preparation indicate a broad range of fluorescence, and a sensitivity of detection in a fresh culture that is not detected with 7-AAD. Fluorescent patterns found in FIG. 11 (i.e. using F(C$_{10}$F)$_9$SH) provide a high resolution and broad dynamic range of three and a half log fluorescence correlated to cellular structures similar to nucleic acids as co-stained by 7-AAD and propidium iodide. Detailed information about cell vitality can be extracted when dye (i.e. F(C$_{10}$F)$_9$ or F(C$_{10}$F)$_9$SH) is used alone and when it is combined with other reagents (i.e. 7-AAD and propidium iodide).

Figure 12:
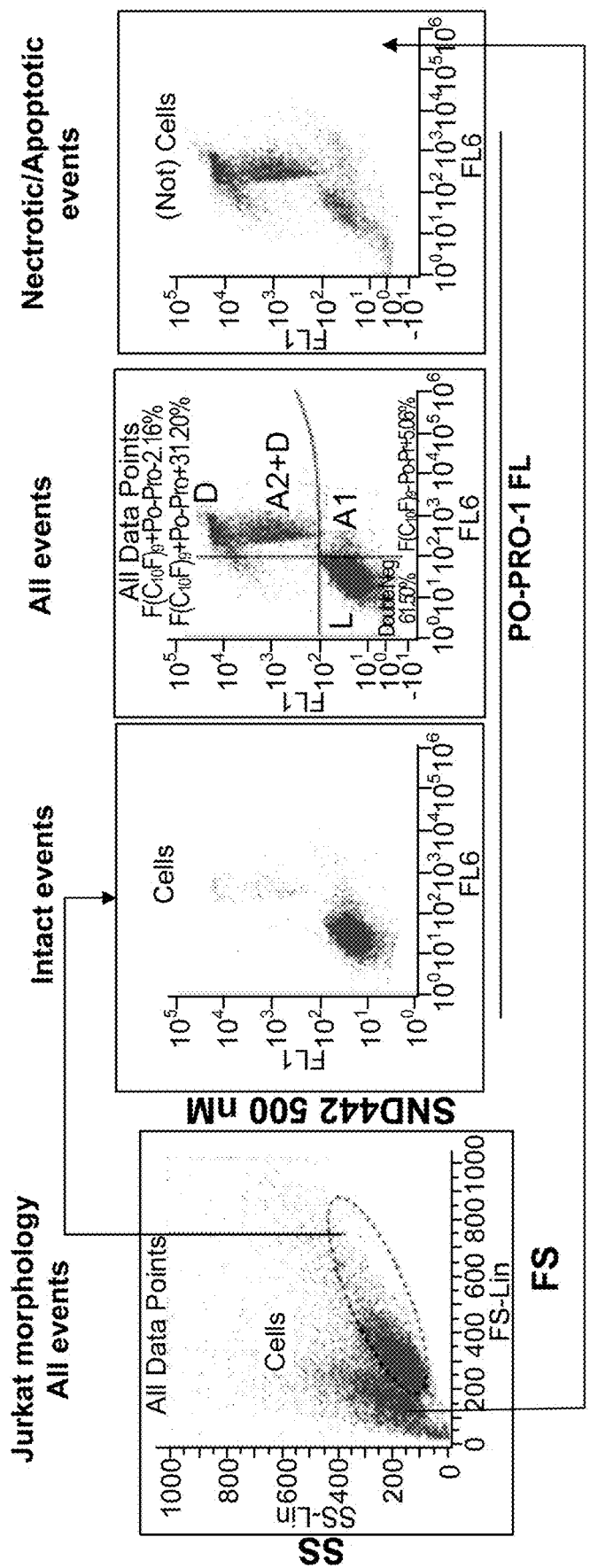
FIG. 12 provides flow cytometry data showing a vitality gradient that correlates to graded states of membrane permeability.

Using this preparation, 4 populations are revealed (live cells [L], apoptotic cells that are not dye positive [A1], cells with low-to-mid brightness [A2], and necrotic cells [D]; see FIG. 12). The fluorescence intensities reveal a gradient that should correlate to graded states of membrane permeability. When intact cells are excluded from the analyses, a detailed pattern of additional live cells/compromised cells emerges that do not fall within an "intact" cell gated by morphology.

Figure 13:
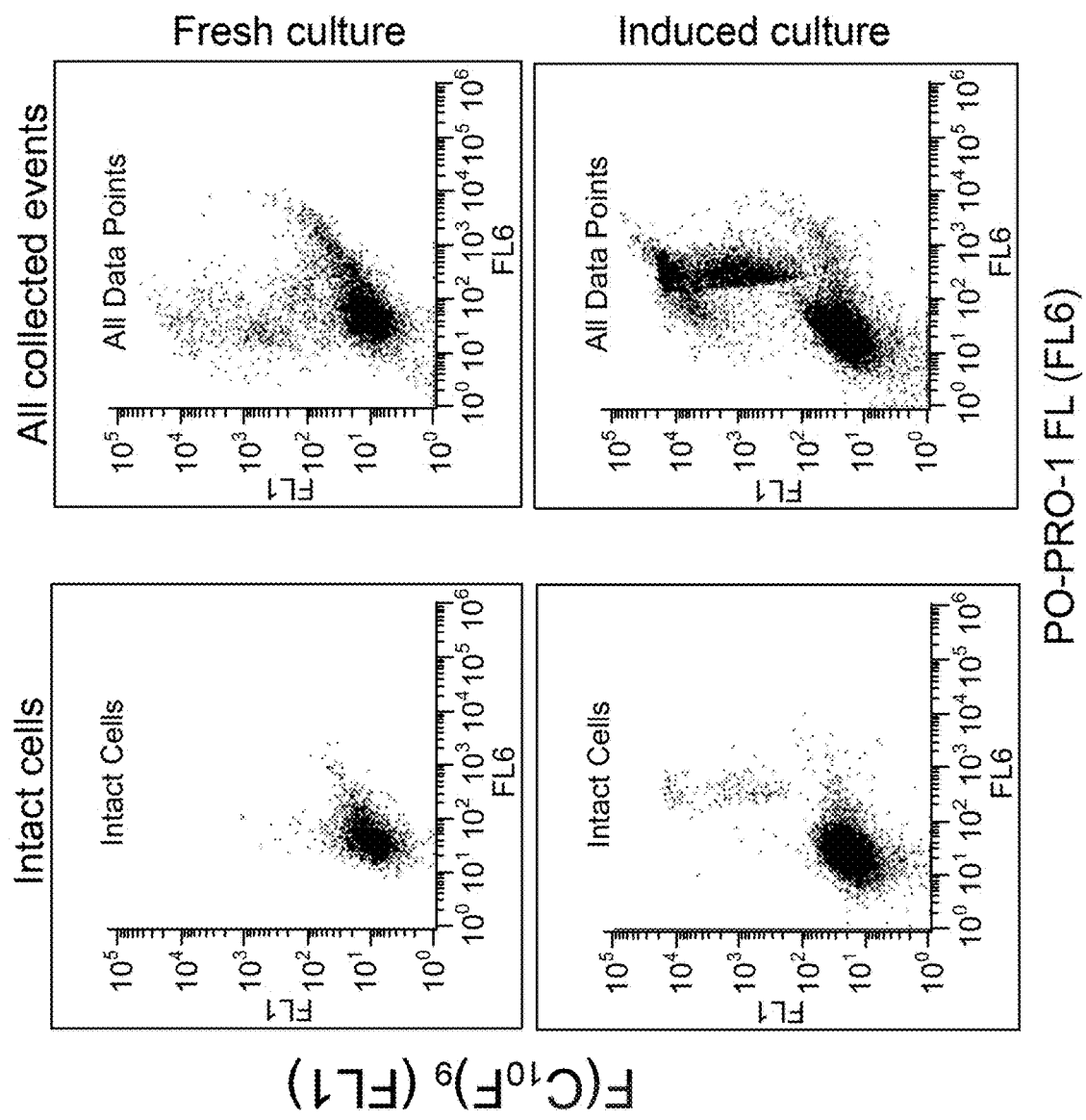
FIG. 13 illustrates sensitive detection of vitality states between two different cultures and morphology interpretations.

FIG. 13 shows fresh culture and sensitive detection of vitality states between two different cultures and two different morphology interpretations of the collected events.

Example 18

Staining of Cells with F(C$_{10}$F)$_9$

F(C$_{10}$F)$_9$ bulk dye used in the preparation described in Example 17 unexpectedly and advantageously stains dead cells much like the amine reactive dye described in Example 16. This indicates that F(C$_{10}$F)$_9$ dye in solution does not need to be functionalized in order to bind. The impact of this discovery on typical live/dead cell protocol would dispense the requirement for a protein free incubation buffer and dramatically increase the ease of use for staining dead cells. Traditional amine reactive (i.e. fixable) dyes require a resuspension of cells in a protein free buffer prior to staining.

Example 19

Patterns and Effects of Dead/Apoptotic Cells

Patterns of mitosis were found in analyzing dead cells. Flow cytometry data obtained using F(C$_{10}$F)$_9$ show patterns that resemble a DNA histogram (see FIGS. 14a-b). In addition, F(C$_{10}$F)$_9$ dye stained cells show a pattern that resembles a proliferation arc (see FIGS. 15a-b). These findings indicate the dyes bind multiple sizes of cellular material that is not an intact cell but correlate to classical interpretations of nucleic acid staining patterns of ploidy. Despite the fact that the dye appears to label "non-intact cells" they are predicted to bind DNA or proteins associated with DNA in fixed and permeabilized cells.

Figures 14A, 14B:
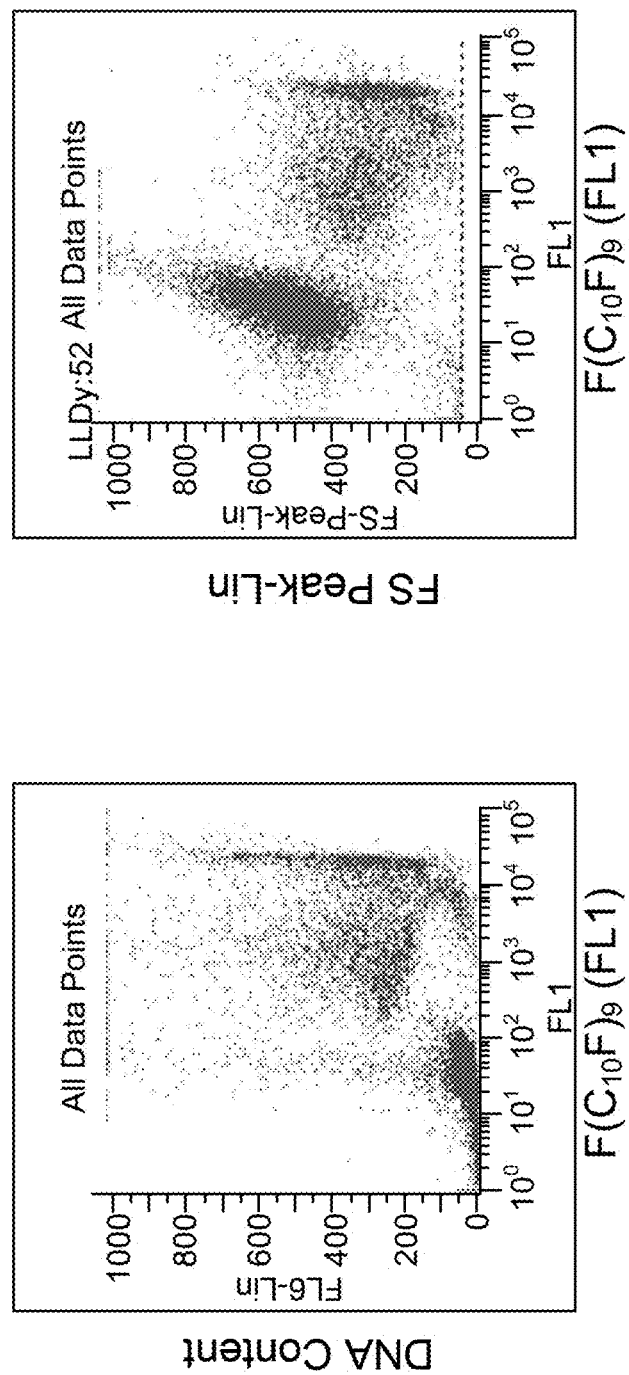
FIGS. 14a and 14b illustrate patterns of mitosis found in dead cells.

Dye staining shows Jurkat cells that express multiple chromosomes and are in a hyper-diploid state (FIGS. 14a-b). Dye stained Jurkat and Ramos cellular material correlates to classical patterns of proliferation (FIGS. 15a-b).

All of the U.S. patents, U.S. patent application publications, U.S. patent applications, foreign patents, foreign patent applications and non-patent publications referred to in this specification, including U.S. provisional patent application Ser. No. 62/159,771, filed May 11, 2015, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound having the following structure

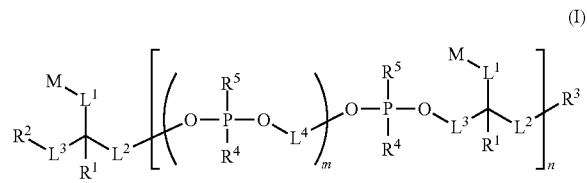

(I)

or a stereoisomer, salt or tautomer thereof, wherein:
M is, at each occurrence, independently a fluorescent or colored moiety comprising three or more aryl or heteroaryl rings, or combinations thereof,
L$^1$, L$^2$ and L$^3$ are, at each occurrence, independently an optional alkylene, alkenylene, alkynylene, heteroalkylene, heteroalkenylene, heteroalkynylene or heteroatomic linker;
L$^4$ is, at each occurrence, independently an alkylene, alkenylene, alkynylene, heteroalkylene, heteroalkenylene or heteroalkynylene linker;
R$^1$ is, at each occurrence, independently H, alkyl or alkoxy;

R² and R³ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O, S, $OR^d$ or $SR^d$; $R_c$ is OH, SH, O, S, $OR^d$, $SR^d$, alkyl, alkoxy, alkylether, alkoxyalkylether, phosphate, thiophosphate, phosphoalkyl, thiophosphoalkyl, phosphoalkylether or thiophosphoalkylether;

$R^4$ is, at each occurrence, independently OH, SH, O, S, $OR^d$ or $SR^d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

$R^d$ is a cation;

m is, at each occurrence, independently an integer of zero or greater, provided that at least one occurrence of m is an integer of three or greater; and n is an integer of one or greater.

2. The compound of claim 1, wherein the compound has the following structure (IA):

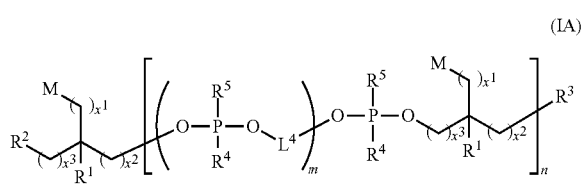

wherein $x^1$, $x^2$ and $x^3$ are, at each occurrence, independently an integer from 0 to 6.

3. The compound of claim 1, wherein the compound has the following structure (IB):

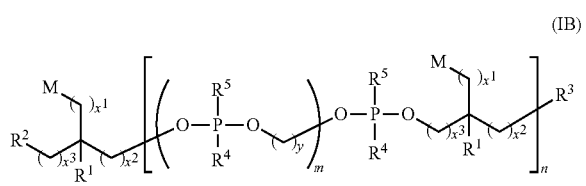

wherein:
$x^1$, $x^2$ and $x^3$ are, at each occurrence, independently an integer from 0 to 6; and
y is an integer from 1 to 6.

4. The compound of claim 1, wherein the compound has one of the following structures (IB') or (IB"):

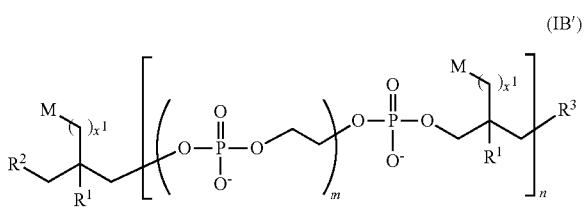

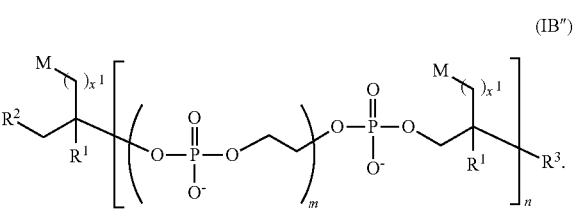

5. The compound of claim 1, wherein R² and R³ are each independently OH or —OP(=$R_a$)($R_b$)$R_c$.

6. The compound of claim 1, wherein one of R² or R³ is OH or —OP(=$R_a$)($R_b$)$R_c$, and the other of R² or R³ is Q or a linker comprising a covalent bond to Q.

7. The compound of claim 1, wherein Q comprises a sulfhydryl, disulfide, activated ester, isothiocyanate, azide, alkyne, alkene, diene, dienophile, acid halide, sulfonyl halide, phosphine, α-haloamide, biotin, amino or a maleimide functional group.

8. The compound of claim 1, wherein Q comprises a moiety selected from Table 1.

9. The compound of claim 1, wherein one of R² or R³ is OH or —OP(=$R_a$)($R_b$)$R_c$, and the other of R² or R³ is a linker comprising a covalent bond to an analyte molecule or a linker comprising a covalent bond to a solid support.

10. The compound of claim 9, wherein the analyte molecule is an enzyme, receptor, receptor ligand, antibody, glycoprotein, aptamer or prion.

11. The compound of claim 1, wherein m is, at each occurrence, independently an integer from 3 to 10.

12. The compound of claim 1, wherein m is, at each occurrence, independently an integer from 7 to 9.

13. The compound of claim 1, wherein M is, at each occurrence, independently fluorescent or colored.

14. The compound of claim 1, wherein M is, at each occurrence, independently a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diazaindacene)phenyl, (bis-fluorophenyl-difluorobora-diazaindacene)phenyl, quaterphenyl, bi-benzothiazole, ter-benzothiazole, bi-naphthyl, bi-anthracyl, squaraine, squarylium, 9,10-ethynylanthracene, ter-naphthyl, p-terphenyl, perylene, azobenzene, phenazine, phenanthroline, thioxanthrene, chrysene, rubrene, coronene, cyanine, perylene imide, perylene amide, coumarin dye, resorufin dye, dipyrromethenboron difluoride dye, ruthenium bipyridyl dye, energy transfer dye, thiazole orange dye, polymethine or N-aryl-1,8-naphthalimide dye moiety.

15. The compound of claim 1, wherein M is, at each occurrence, independently pyrene, perylene, perylene monoimide or 6-FAM or derivative thereof.
16. The compound of claim 1, wherein M, at each occurrence, independently has one of the following structures:
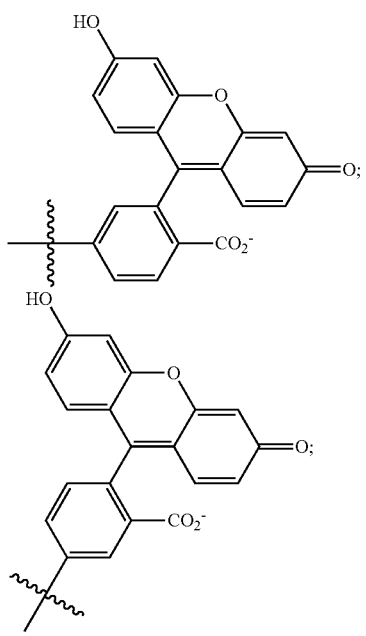
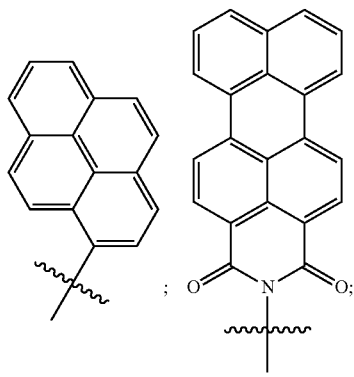
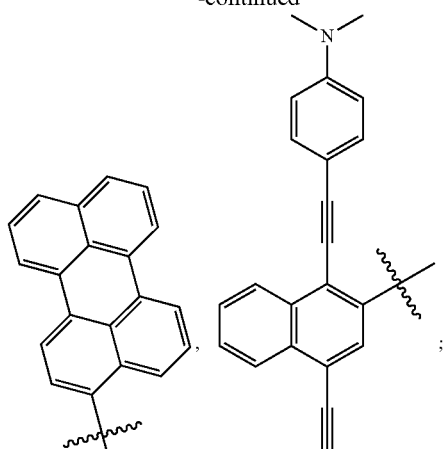
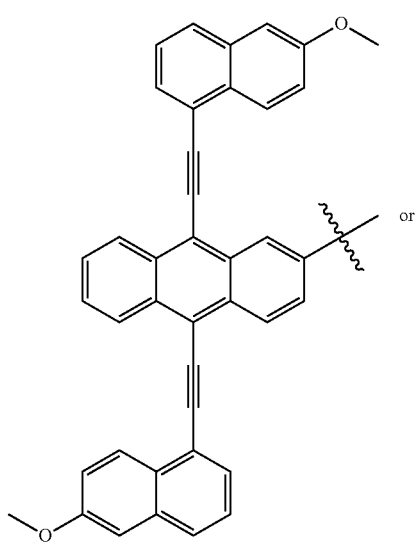
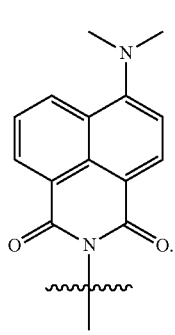

17. The compound of claim 1, wherein the compound is selected from one of the following structures:
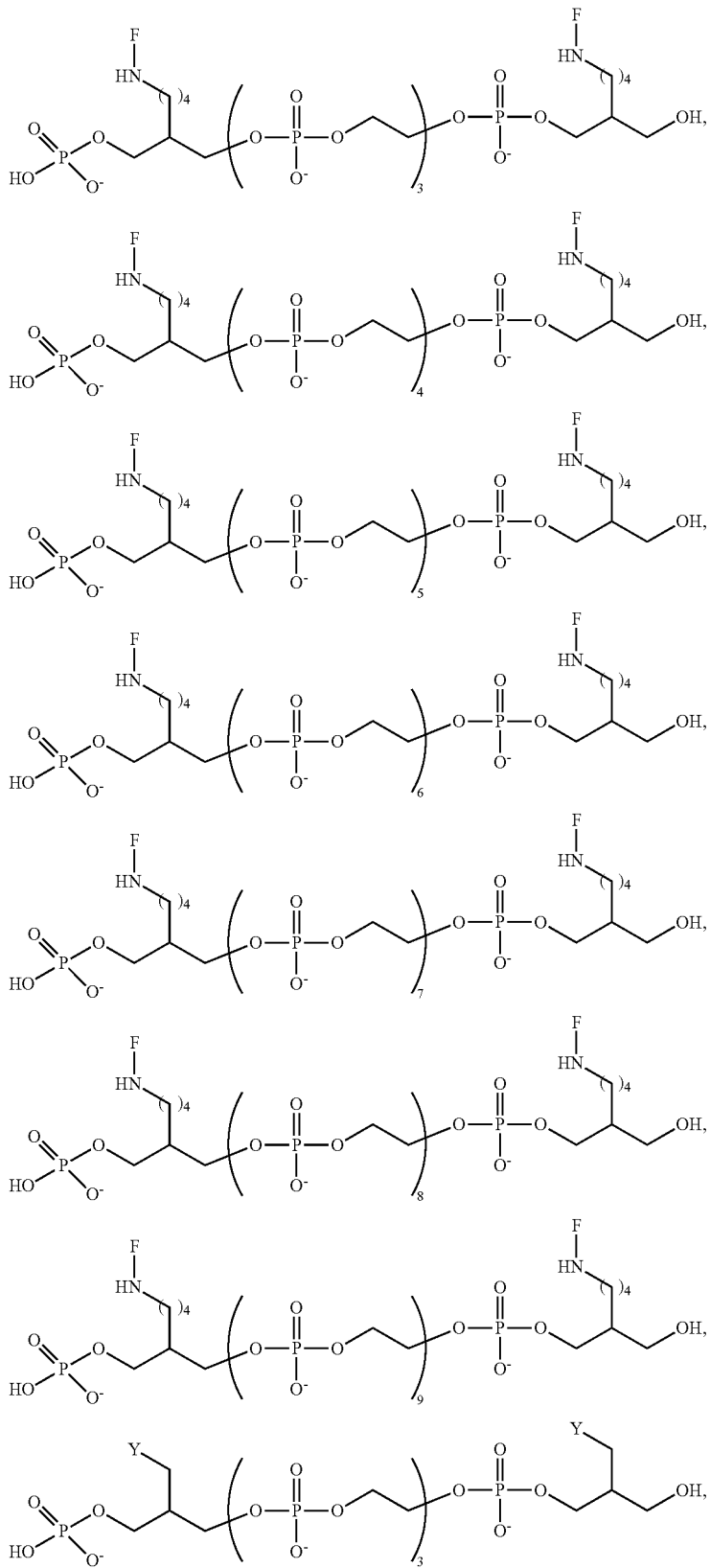

-continued
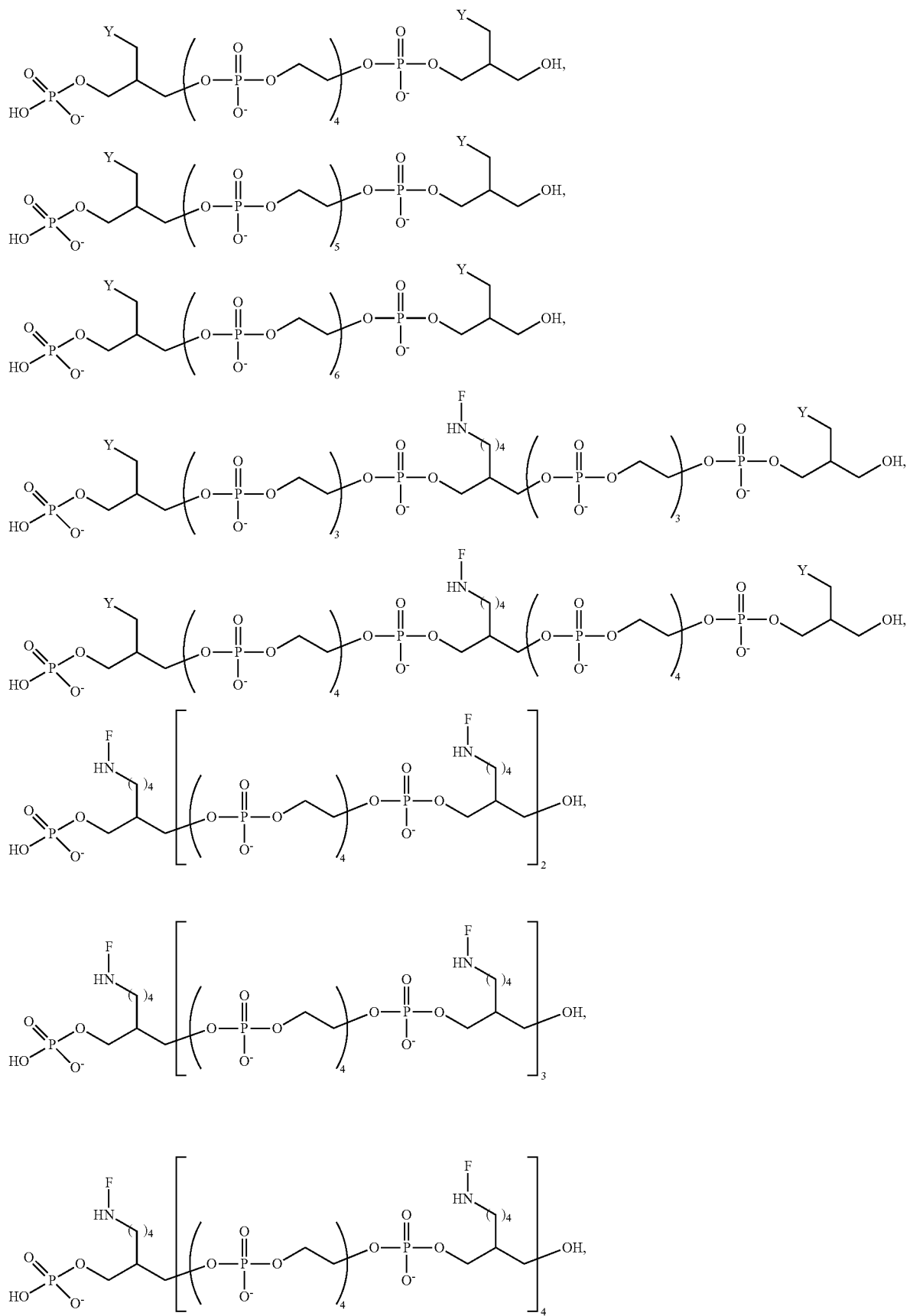

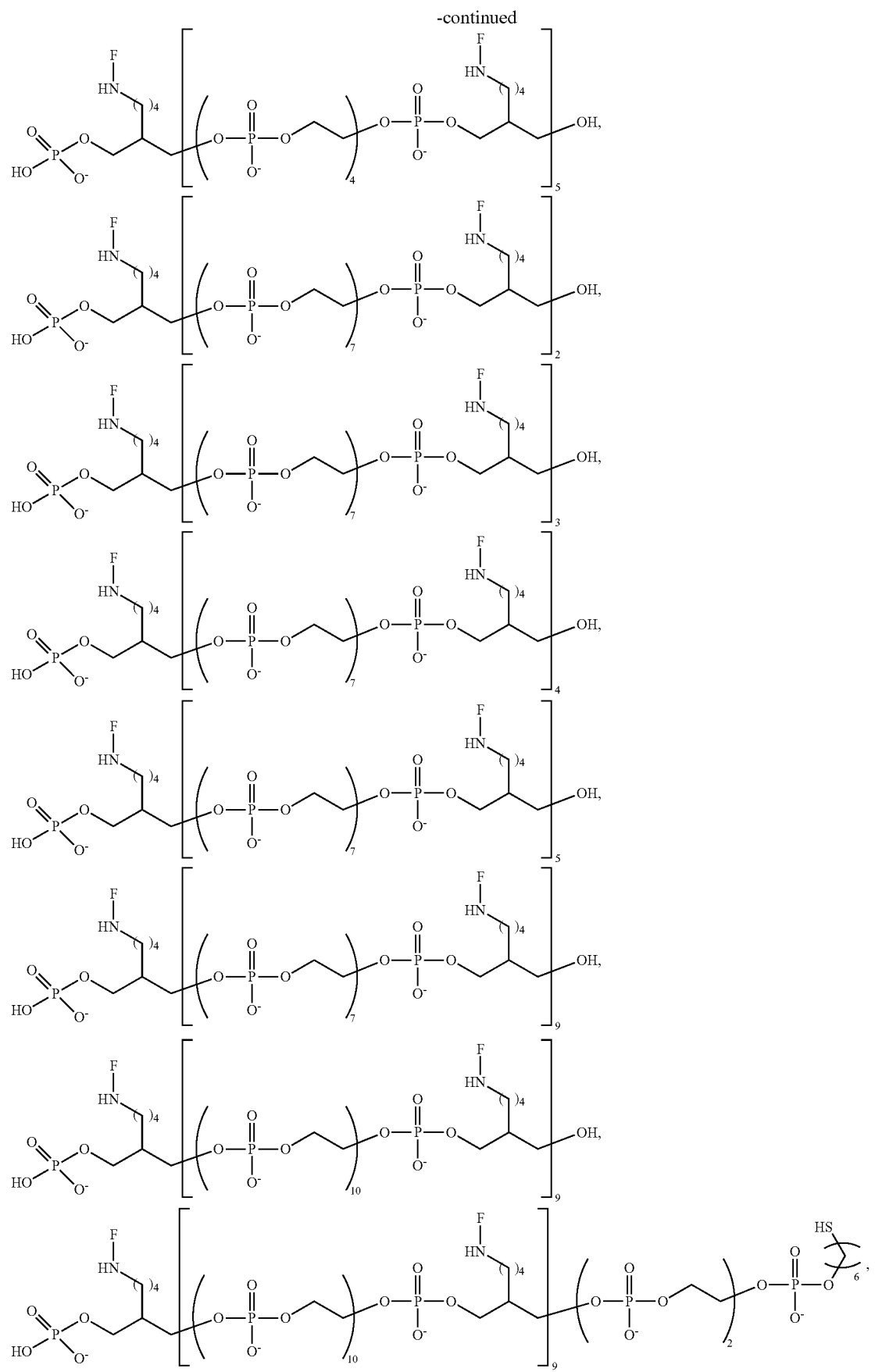
-continued

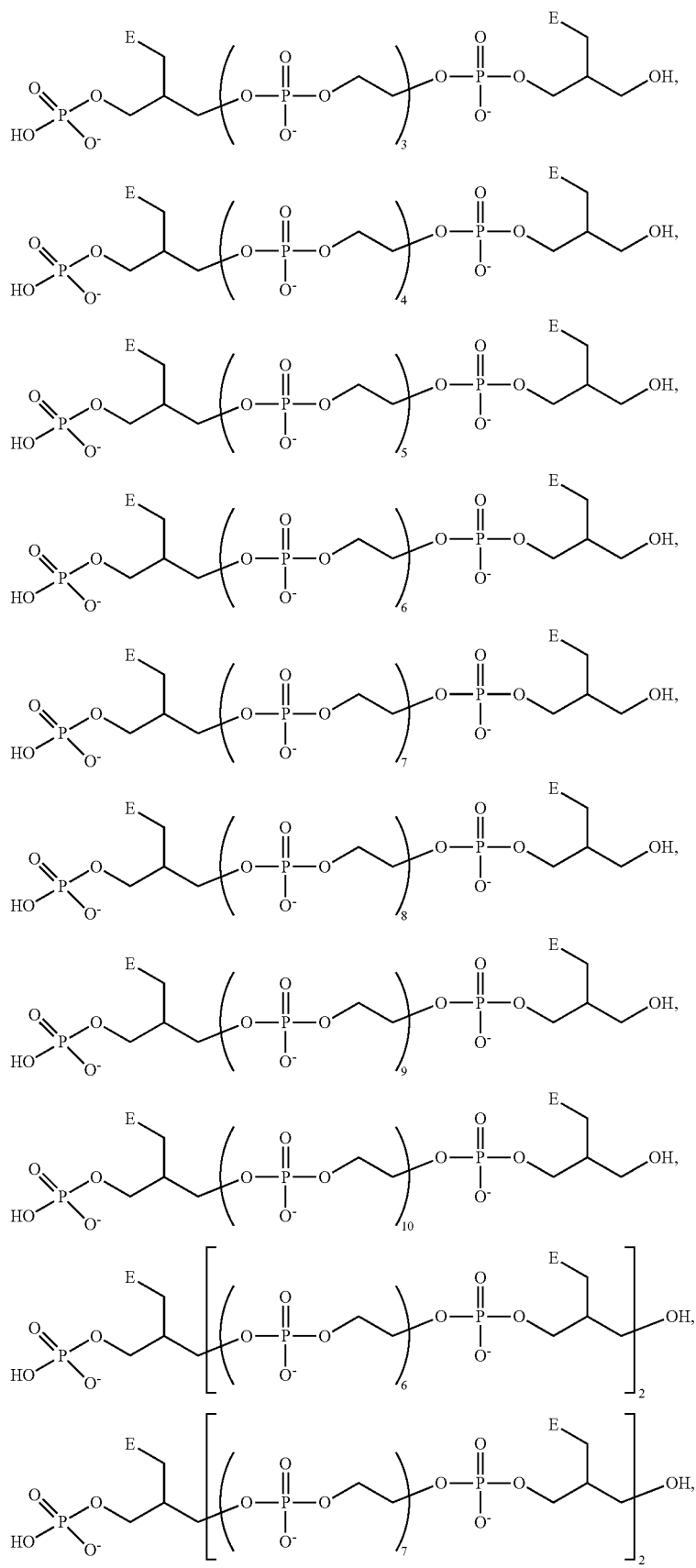

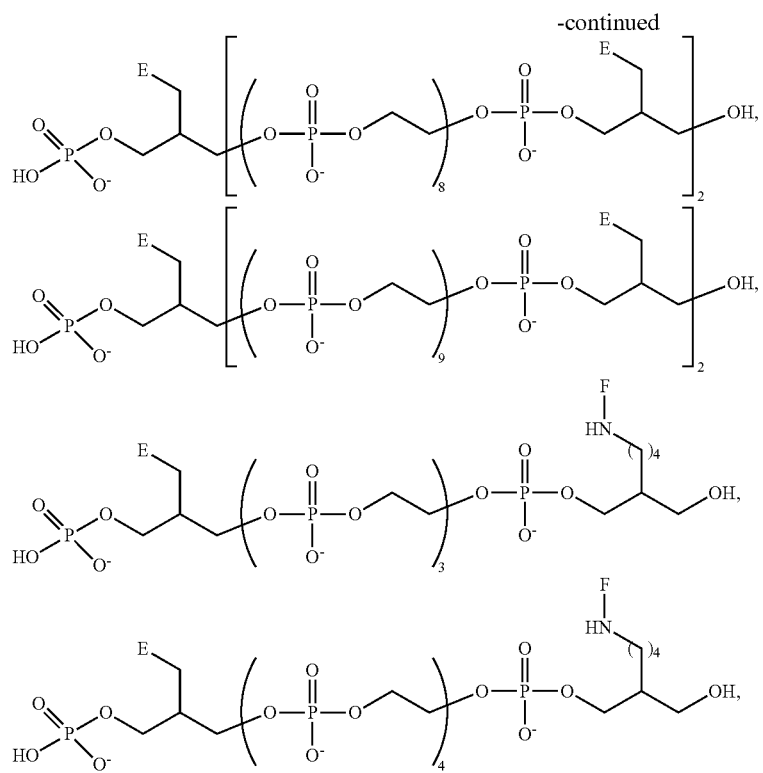
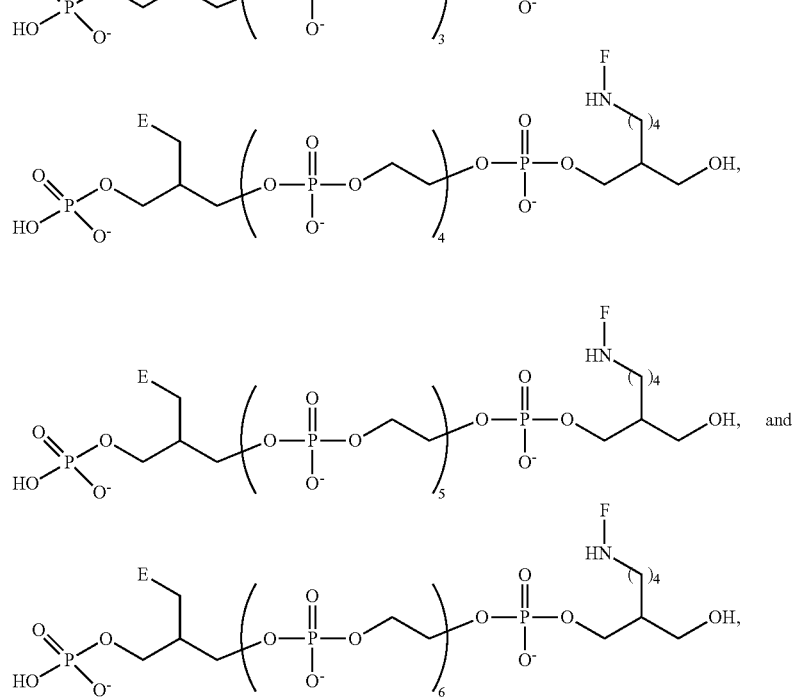
wherein F, E and Y have the following structures:
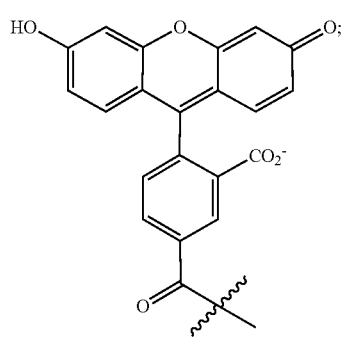
"F"
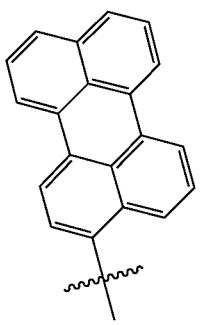
"E" and -continued

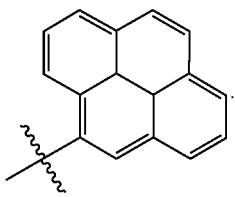

"Y"

18. A method of staining a sample, comprising adding to said sample the compound of claim 1 in an amount sufficient to produce an optical response when said sample is illuminated at an appropriate wavelength.

19. A method for visually detecting an analyte molecule, the method comprising:
   (a) providing the compound of claim 1, wherein $R^2$ or $R^3$ is a linker comprising a covalent bond to the analyte molecule; and
   (b) detecting the compound by its visible properties.

20. A method for visually detecting an analyte molecule, the method comprising:
   (a) admixing the compound of claim 1, wherein $R^2$ or $R^3$ is Q or a linker comprising a covalent bond to Q, with the analyte molecule;
   (b) forming a conjugate of the compound and the analyte molecule; and
   (c) detecting the conjugate by its visible properties.

21. A composition comprising the compound of claim 1 and one or more analyte molecules.

22. A method for determining the presence of dead cells in a sample, the method comprising contacting the sample with a compound of claim 1, thereby binding or associating the compound with the dead cells, and observing a fluorescent signal from the compound bound or associated with the dead cells.

\* \* \* \* \*

UNITED STATES PATENT AND TRADEMARK OFFICE
CERTIFICATE OF CORRECTION

PATENT NO. : 10,865,310 B2
APPLICATION NO. : 15/543827
DATED : December 15, 2020
INVENTOR(S) : Tracy Matray et al.

Page 1 of 1

It is certified that error appears in the above-identified patent and that said Letters Patent is hereby corrected as shown below:

In the Claims

Column 62, Claim 1, Line 58:
"thereof," should be: --thereof;--.

Column 63, Claim 1, Line 8:
"OH, SH, O, S, $OR^d$ or $SR^d$; $R_c$ is OH, SH, O, S, $OR^d$," should read: --OH, SH, O-, S-, $OR^d$ or $SR^d$; $R_c$ is OH, SH, O-, S-, $OR^d$,--.

Column 63, Claim 1, Line 13:
"OH, SH, O, S," should read: --OH, SH, O-, S-,--.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*